US012680126B2

(12) United States Patent
Stowe

(10) Patent No.: US 12,680,126 B2
(45) Date of Patent: Jul. 14, 2026

(54) METHODS AND REAGENTS FOR RAPID DETECTION OF PATHOGENS IN BIOLOGICAL SAMPLES

(71) Applicant: Microgen Laboratories, LaMarque, TX (US)

(72) Inventor: Raymond P. Stowe, Galveston, TX (US)

(73) Assignee: Microgen Laboratories, LaMarque, TX (US)

( * ) Notice: Subject to any disclaimer, the term of this patent is extended or adjusted under 35 U.S.C. 154(b) by 646 days.

(21) Appl. No.: 18/043,306

(22) PCT Filed: Aug. 25, 2021

(86) PCT No.: PCT/US2021/047543
§ 371 (c)(1),
(2) Date: Feb. 27, 2023

(87) PCT Pub. No.: WO2022/046900
PCT Pub. Date: Mar. 3, 2022

(65) Prior Publication Data
US 2023/0332216 A1        Oct. 19, 2023

Related U.S. Application Data

(60) Provisional application No. 63/070,216, filed on Aug. 25, 2020.

(51) Int. Cl.
| | |
|---|---|
| *C12P 19/34* | (2006.01) |
| *C12Q 1/6806* | (2018.01) |
| *C12Q 1/6844* | (2018.01) |
| *C12Q 1/70* | (2006.01) |

(52) U.S. Cl.
CPC ......... *C12Q 1/6844* (2013.01); *C12Q 1/6806* (2013.01); *C12Q 1/70* (2013.01)

(58) Field of Classification Search
CPC .................................. C12Q 1/689; C12Q 1/70
See application file for complete search history.

(56) References Cited

U.S. PATENT DOCUMENTS

| | | | |
|---|---|---|---|
| 2006/0257874 A1* | 11/2006 | Tisi ...................... | C12Q 1/6851 |
| | | | 435/6.14 |
| 2007/0015185 A1 | 1/2007 | Basehore et al. | |
| 2009/0155777 A1* | 6/2009 | Yang .................... | C12Q 1/6806 |
| | | | 435/6.1 |
| 2010/0099150 A1 | 4/2010 | Fang et al. | |
| 2013/0210016 A1* | 8/2013 | Dugan ................. | C12Q 1/6806 |
| | | | 435/6.12 |
| 2016/0289752 A1* | 10/2016 | Bamford .............. | C12Q 1/6858 |
| 2018/0274022 A1* | 9/2018 | Inada ................... | C12Q 1/6853 |

FOREIGN PATENT DOCUMENTS

| | | | |
|---|---|---|---|
| JP | 2018007580 A | * | 1/2018 |

OTHER PUBLICATIONS

International Search Report and Written Opinion received in PCT/US21/47543, mailed on Feb. 8, 2022 (14 pages).

* cited by examiner

*Primary Examiner* — Kenneth R Horlick
(74) *Attorney, Agent, or Firm* — Torrey Pines Law Group, PC

(57) ABSTRACT

Methods and compositions for rapid detection of pathogens in biological samples, such as saliva or a nasal swab, are disclosed. Nucleic acid molecules from pathogens can be stabilized at room temperature for several days in a transport solution, followed by their amplification without prior extraction. An optimized isothermal amplification method and the amplification solution are also disclosed, allowing for reducing a threshold time for a positive sample. The methods and compositions are suitable for detection of a variety of pathogens, including enveloped viruses, such as Cytomegalovirus or SARS-CoV-2 virus, and pathogenic microorganisms.

17 Claims, 18 Drawing Sheets

Specification includes a Sequence Listing.

15-25 minutes
8 Test Results

8 Strip Tubes

Saliva or Nasal Swab
In Transport Buffer 15-25 minutes
96 Test Results

96 Well Plate 10 seconds - 96 Well Plate
1 minute - 5 Plates 25 minutes
96 Well Heat Blocks Take 6mm Punch & Place in PTM Mix for 20sec Add Inoculated PTM to CMV and Positive Control Tubes

METHODS AND REAGENTS FOR RAPID DETECTION OF PATHOGENS IN BIOLOGICAL SAMPLES

CROSS-REFERENCE TO RELATED APPLICATIONS

This application is a National Stage Entry of PCT Application Ser. No. PCT/US21/47543, filed on Aug. 25, 2021, which claims priority to U.S. provisional application 63/070, 216, filed Aug. 25, 2020. The disclosures and contents of the above-referenced applications are incorporated by reference in their entireties for all purposes.

STATEMENT REGARDING FEDERALLY SPONSORED RESEARCH OR DEVELOPMENT

This invention was made with Government support under R43A1152629 awarded by the National Institutes of Health. The Government has certain rights in the invention.

SEQUENCE LISTING ON ASCII TEXT

This patent application file contains a Sequence Listing submitted in computer readable ASCII text format (file name: MICR-01-PCT1 SeqListing.txt, date recorded: Aug. 20, 2021, size: 7,385 bytes). The Sequence Listing, which is a part of the present disclosure, includes a computer readable form and a written sequence listing comprising nucleotide and/or amino acid sequences of the present invention. The sequence listing information recorded in computer readable form is identical to the written sequence listing. The content of the Sequence Listing file is incorporated herein by reference in its entirety.

TECHNICAL FIELD

Traditional methods to detect infections, including tissue culture and shell vial, are highly labor-intensive and require expensive equipment and dedicated laboratory space. Recent years have seen the development and deployment of NA technologies such as real-time polymerase chain reaction (PCR) that quantitate pathogen nucleic acids from clinical samples. PCR-based methods have been used for more than 30 years in research laboratories; however, the requirement for trained personnel, DNA isolation steps, time-consuming thermal cycling, and relatively expensive equipment limit their suitability for POC use. As a result, it requires 3-7 days to determine if an individual is infected through biospecimens sent to reference laboratories, resulting in a significant delay in diagnosis and initiation of treatment. An easy to use POC test to detect infections in multiple sample types (e.g., nasal or saliva swab, urine, CSF) without upfront sample manipulation would be transformative, allowing rapid determination of infection and prompt initiation of treatment.

Outbreaks of novel virus infections among people are always of public health concern. The risk to the general public from these outbreaks depends on characteristics of the virus, including how well it spreads between people; the severity of resulting illness; and the medical or other measures available to control the impact of the virus. For COVID-19 pandemic, reported illnesses have ranged from very mild (including some with no reported symptoms) to severe, including illness resulting in death. That this disease has caused severe illness, including illness resulting in death is concerning, especially since it has also shown sustained person-to-person spread in several places.

As realized during the COVID-19 crisis, early problems with population screening emerged including: 1) a shortage of RNA isolation reagents, 2) a lack of test instruments, and 3) a shortage of viral transport media. In addition, manufacturers of many EUA-approved tests (e.g., Abbot ID NOW) could not keep up with the demand leading to shortage of tests for the U.S. Moreover, significant limitations when using these tests for mass screening became apparent; for instance, the Abbot ID NOW was only able to run ~17 samples per day and had a 30% false negative rate (personnel communication, Dr. Hunter Hammill MD, OB-GYN in Houston, TX). Thus, it is clear that currently available tests cannot address this challenge.

SUMMARY

The present teachings include methods for amplifying a nucleic acid molecule of a pathogen contained in a biological sample, the method comprising: (a) obtaining a stabilized sample, the stabilized sample comprising the biological sample and a transport solution, wherein the transport solution comprises a non-ionic or zwitterionic detergent at a concentration of 2 to 32 percent (vol./vol.), and wherein the transport solution stabilizes the nucleic acid molecule in the stabilized sample at room temperature; (b) mixing the stabilized sample with an amplification solution without prior extraction of the nucleic acid molecule present in the stabilized sample to form an amplification reaction mixture, wherein the amplification reaction mixture comprises:

a buffering agent that has a pH between about 5 and about 11;

serum albumin at a concentration of 100 μM to 500 μM;

the non-ionic or zwitterionic detergent at a concentration of 1 to 16 percent (vol./vol.), dNTPs, a DNA polymerase enzyme having a strand displacement activity, and at least one pair of primers that target the nucleic acid molecule; and (c) subjecting the amplification reaction mixture to an isothermal amplification, wherein the isothermal amplification amplifies the nucleic acid molecule.

The disclosed optimized isothermal amplification method and the amplification solution allows for accelerated detection of a pathogen.

dNTPs is a mixture of four nucleotides that includes dATG, dCTP, dGTP, dTTP, which are building blocks for synthesis of new strands of DNA.

In some embodiments, the amplification reaction mixture further comprises one or more salts at concentration(s) optimal for DNA polymerase to amplify the nucleic acid molecule. Exact salt(s) and their concentrations depend on particular amplification method and particular DNA polymerase enzyme utilized.

In accordance with a further aspect, the transport solution further comprises a buffering agent that has a pH between about 5 and about 11, and a chelating agent.

In accordance with yet another aspect, the method comprises contacting the sample with a transport solution comprising a non-ionic or zwitterionic detergent at a concentration of 2 to 32 percent (vol./vol.), to form a stabilized sample, wherein the transport solution stabilizes the nucleic acid molecule in the stabilized sample at room temperature.

As used herein, the term "stabilizes a nucleic acid molecule" refers to stabilization of structure of the nucleic acid molecule, preventing degradation of the nucleic acid molecule to the extent that the nucleic acid molecule can be identified after storage in the transport solution by one of the amplification methods, such as an isothermal amplification method, or a PCR.

In some embodiments of the invention, the transport solution containing a non-ionic or zwitterionic detergent at a concentration of 2 to 32 percent (vol./vol.) stabilizes a nucleic acid molecule within a biological sample for at least 2 days at room temperature (as used herein, room temperature refers to any temperature within 18-25° C. range, for example, 23° C.). In some preferred embodiments of the invention, the transport solution containing a non-ionic or zwitterionic detergent at a concentration of 2 to 32 percent (vol./vol.) stabilizes a nucleic acid molecule within a biological sample for at least 5, 10, 20, 28, 40 or 50 days at room temperature.

In accordance with yet another aspect, the transport solution stabilizes the nucleic acid in the stabilized sample at room temperature for at least four weeks.

In accordance with yet another aspect, the pathogen is selected from the group consisting of: an enveloped virus, pathogenic yeast and bacteria.

In accordance with yet another aspect, the enveloped virus is Cytomegalovirus or SARS-CoV-2 virus.

In accordance with yet another aspect, the amplification reaction mixture further comprises (i) MgSO4 at a concentration of 0.5 mM to 3 mM, or (ii) a second non-ionic or zwitterionic detergent at a concentration of 0.1% to 5%. In accordance with yet another aspect, the amplification reaction mixture further comprises a second non-ionic or zwitterionic detergent at a concentration of 0.3% to 1%.

In accordance with yet another aspect, the amplification reaction mixture comprises at least two pairs of primers that target the nucleic acid molecule. In accordance with yet another aspect, the isothermal amplification is a strand displacement amplification, a multiple displacement amplification, a recombinase polymerase amplification, a helicase dependent amplification, a rolling circle amplification, or a loop-mediated isothermal amplification.

In accordance with yet another aspect, the nucleic acid molecule is a ribonucleic acid (RNA) and a corresponding DNA molecule is produced from the RNA by a reverse transcriptase enzyme prior to or simultaneously with the isothermal amplification.

In accordance with yet another aspect, the biological sample contains a pathogen, and it is selected from the list consisting of saliva, a nasal swab, urine, lesion exudate, dried blood spot, blood, plasma/serum, mucus, vaginal fluid or another type of bodily fluid. In other embodiments, the biological sample contains cells, or comprises a cell extract. In other embodiments, the biological sample contains yeast or bacterial cells.

In accordance with yet another aspect, the transport solution consists essentially of the non-ionic or zwitterionic detergent at a concentration of 2 to 32 percent (vol./vol.).

In accordance with yet another aspect, the non-ionic or zwitterionic detergent is selected from the group consisting of: Triton X-100, NP-40, Triton X-45, Tween 20, Tween 80, CHAPS, CHAPSO, and a mixture thereof. In accordance with yet another aspect, the non-ionic or zwitterionic detergent is a mixture of at least two different non-ionic or zwitterionic detergents selected from the group consisting of: Triton X-100, NP-40, Triton X-45, Tween 20, Tween 80, CHAPS and CHAPSO.

In accordance with yet another aspect, the isothermal amplification amplifies the nucleic acid molecule in less than 30 min.

In accordance with yet another aspect, the non-ionic or zwitterionic detergent is present in the amplification reaction mixture at a concentration of 2 to 5 percent (vol./vol.).

In some embodiments, serum albumin is a human serum albumin or bovine serum albumin.

In accordance with a further aspect, a method for detecting a presence of a pathogen in a biological sample in less than 30 min is provided, comprising:

(a) obtaining a stabilized sample, the stabilized sample comprising the biological sample and a transport solution, wherein the transport solution comprises a non-ionic or zwitterionic detergent at a concentration of 2 to 32 percent (vol./vol.), and wherein the transport solution stabilizes the nucleic acid molecule in the stabilized sample at room temperature;

(b) mixing the stabilized sample with an amplification solution without prior extraction of the nucleic acid molecule present in the stabilized sample to form an amplification reaction mixture, wherein the amplification reaction mixture comprises:

a buffering agent that has a pH between about 5 and about 11;

serum albumin at a concentration of 100 μM to 500 μM;

the non-ionic or zwitterionic detergent at a concentration of 1 to 16 percent (vol./vol.), dNTPs, a DNA polymerase enzyme having a strand displacement activity, and at least one pair of primers that target the nucleic acid molecule; and (c) subjecting the amplification reaction mixture to an isothermal amplification, wherein the isothermal amplification amplifies the nucleic acid molecule of the pathogen;

(d) detecting a presence of the amplified nucleic acid molecule by at least one of the following: colorimetric readout, fluorescent readout, lateral flow assay, a biosensor, wherein the presence of the amplified nucleic acid molecule indicates the presence of the pathogen in the biological sample.

In accordance with a further aspect, a method for amplifying a nucleic acid molecule of a pathogen contained in a biological sample is provided, the method comprising: (a) obtaining a stabilized sample, the stabilized sample consisting essentially of the biological sample and a transport solution, wherein the transport solution consists essentially of a non-ionic or zwitterionic detergent at a concentration of 2 to 32 percent (vol./vol.), and wherein the transport solution stabilizes the nucleic acid molecule in the stabilized sample at room temperature; (b) mixing the stabilized sample with an amplification solution without prior extraction of the nucleic acid molecule present in the stabilized sample to form an amplification reaction mixture comprising the non-ionic or zwitterionic detergent at a concentration of 1 to 16 percent (vol./vol.); (c) subjecting the amplification reaction mixture to an isothermal amplification or to a polymerase chain reaction (PCR), wherein the isothermal amplification or PCR amplifies the nucleic acid molecule.

In a preferred embodiment, the non-ionic or zwitterionic detergent can be selected from the group consisting of: Triton X-100, NP-40, Triton X-45, Tween 20, Tween 80, CHAPS, CHAPSO, and a mixture thereof.

In another preferred embodiment, the non-ionic or zwitterionic detergent is present in the amplification reaction mixture at a concentration of 2 to 5 percent (vol./vol.).

In yet another preferred embodiment, the transport solution stabilizes the nucleic acid in the stabilized sample at room temperature for at least four weeks.

In yet another embodiment, the nucleic acid molecule is a ribonucleic acid (RNA) and a corresponding DNA molecule is produced from the RNA by adding a reverse transcriptase enzyme prior to or simultaneously with the step (c).

In yet another preferred embodiment, the isothermal amplification is used in step (c), and the isothermal amplification amplifies the nucleic acid molecule in less than 30 min.

In various embodiments of the invention, different DNA polymerases known to a skilled person, can be utilized for the disclosed amplification reactions. In preferred embodiments of the invention, when isothermal amplification reactions are utilized, such as LAMP, a DNA polymerase enzyme having a strong strand displacement and replicative activity is used for the disclosed amplification reactions. Examples of such DNA polymerase enzymes include, but not limited to, Klenow exo-, Bsu large fragment, phi29 the large fragment of Bst DNA polymerase, an engineered thermostable polymerase having a strong strand displacement activity, such as, for example, Taq DNA polymerase mutant (Ignatov K B, et al., A strong strand displacement activity of thermostable DNA polymerase markedly improves the results of DNA amplification. Biotechniques. 2014 Aug. 1; 57(2):81-7). In other embodiments of the invention, when a PCR is used for amplification of nucleic acids, a DNA polymerase enzyme without strand displacement activity can be utilized, such as Taq DNA polymerase, or other known polymerases.

In accordance with a further aspect, a reagent kit for amplifying a nucleic acid molecule is provided, comprising: (a) a transport solution comprises a non-ionic or zwitterionic detergent at a concentration of 2 to 32 percent (vol./vol.), wherein the transport solution stabilizes a nucleic acid molecule at room temperature; and (b) an amplification solution that when mixed with the transport solution and the nucleic acid molecule forms an amplification reaction mixture comprising:

(i) a buffering agent that has a pH between about 5 and about 11;
  (ii) the non-ionic or zwitterionic detergent at a concentration of 1 to 16 percent (vol./vol.);
  (iii) serum albumin at a concentration of 100 µM to 500 µM.

In a preferred embodiment, the amplification reaction mixture further comprises (i) MgSO4 at a concentration of 0.5 mM to 3 mM; or (iii) a second non-ionic or zwitterionic detergent at a concentration of 0.1% to 5%.

In accordance with yet another aspect, the transport solution of the reagent kit consists essentially of the non-ionic or zwitterionic detergent at a concentration of 2 to 32 percent (vol./vol.).

In accordance with yet another aspect, the transport solution of the reagent kit consists essentially of the non-ionic or zwitterionic detergent at a concentration of 2 to 32 percent (vol./vol.) and a buffering agent that has a pH between about 5 and about 11.

In another preferred embodiment, the non-ionic or zwitterionic detergent is selected from the group consisting of: Triton X-100, NP-40, Triton X-45, Tween 20, Tween 80, CHAPS, CHAPSO, and a mixture thereof.

In another preferred embodiment, the non-ionic or zwitterionic detergent is present in the amplification reaction mixture at a concentration of 2 to 5 percent (vol./vol.).

In another embodiment, the second non-ionic or zwitterionic detergent is selected from the group consisting of:

Triton X-100, NP-40, Triton X-45, Tween 20, Tween 80, CHAPS, CHAPSO, and a mixture thereof.

These and other features, aspects and advantages of the present teachings will become better understood with reference to the following description, examples and appended claims.

BRIEF DESCRIPTION OF THE DRAWINGS

Those of skill in the art will understand that the drawings, described below, are for illustrative purposes only. The drawings are not intended to limit the scope of the present teachings in any way. Standard amplification reactions used to generate the provided Figures, unless otherwise stated, were assembled by mixing the Amplification Solution with the pathogen-containing transport solution (TS) containing 2% Triton X-100 in 1:1 (Vol/Vol) ratio; thus, amplification reaction mixtures contained 1% Triton X-100. In some particular examples, amplification reaction mixtures contained 2-16% Triton X-100. Reactions were carried out in a total 25 µl reaction volume containing approximately 50 pmol each of the forward and backward internal primers, 25 pmol each of forward and backward loop primers in the amplification reaction mixture having 20 mM Tris-HCl pH8.8, 10 mM (NH4)2SO4, 2 mM MgSO4, 50 mM KCl, 1.4 mM dNTPs, 01% Tween 20, 8 units of the Bst DNA polymerase (NEB), 300 uM BSA, 1× EvaGreen dye, and 1% Triton X-100 from the transport solution (TS). Positive and negative controls were included in each run, and all precautions to prevent cross-contamination were observed. The optimum temperature for the amplification reaction was 68° C. After mixing and incubating for 2 min, amplification and preliminary detection (one minute read increments) was cal ied out in a single step using a MIX3005P instrument and software. Alternatively, a portable isothermal instrument was used (EseQuant TS2 or Axxin T8).

As shown in FIG. 16D, the CMV+ DBS sample (line 1) was positive while the CMV-DBS sample (line 2) was negative. The positive control (line 3) also showed positive amplification.

The LAMP assay reactions were carried out as described in Example 11. The amplification results for EBV pathogen kept in the TS before amplification using three different buffer conditions are presented: Reaction 1—buffer with ammonium sulfate and Tween-20; Reaction 2—buffer with Tween-20 but no ammonium sulfate; Reaction 3—buffer with no Tween-20 and no ammonium sulfate.

Figure 18A:
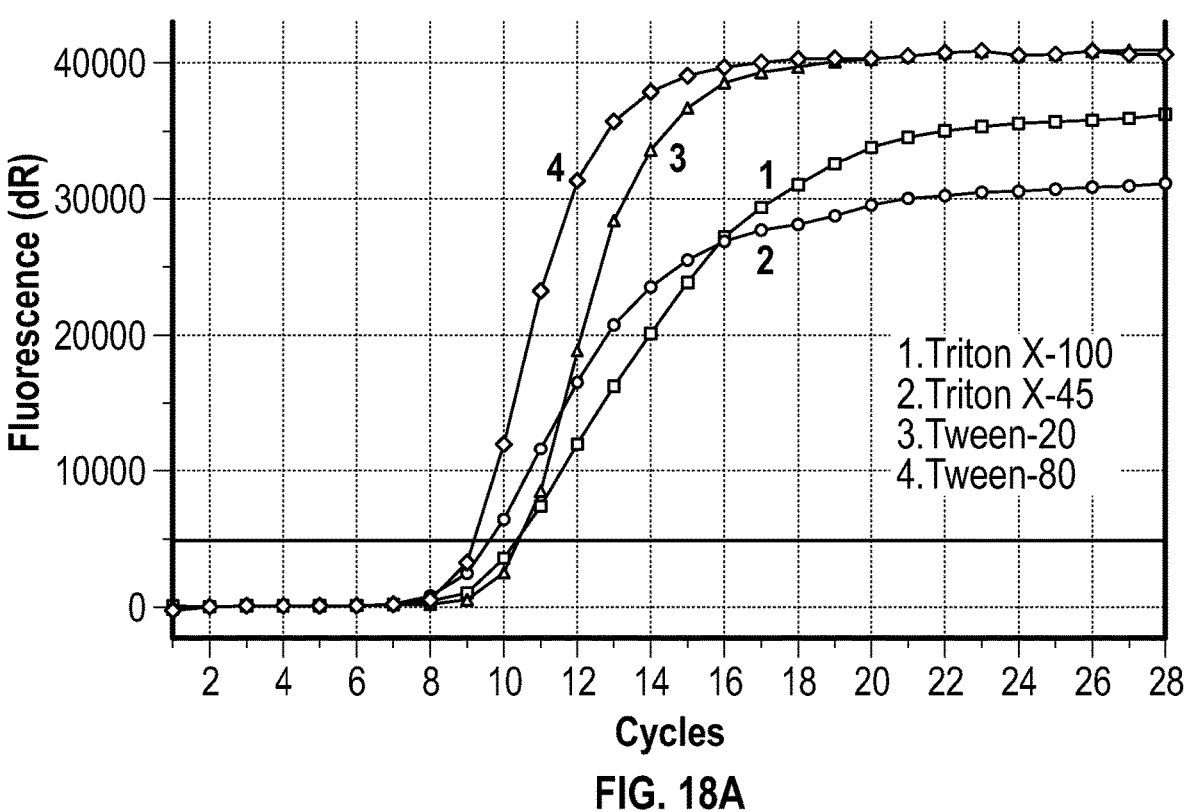
Figure 18B:
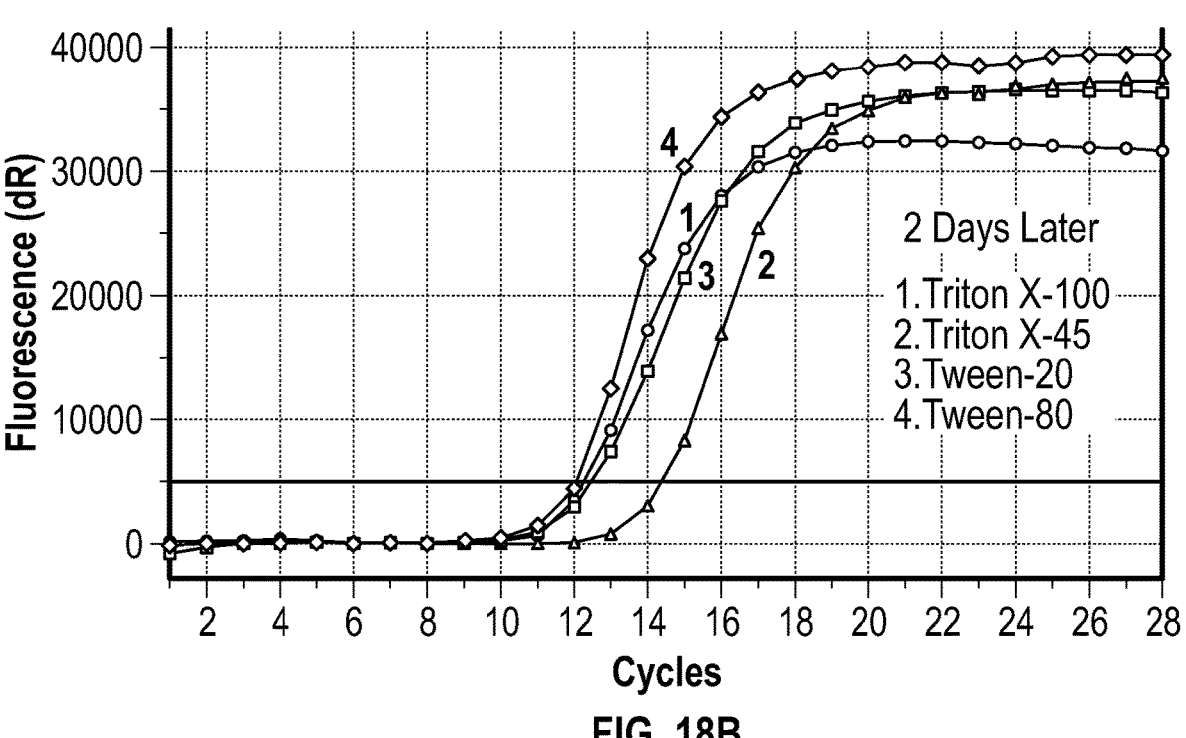

FIG. 18A-B. Evaluating influence of different detergents used in the transport solution (TS) and the amplification reaction mixture on LAMP amplification efficiency of the HSV-1 pathogen from clinical samples.

Four different non-ionic detergents present in the TS (concentration for each detergent was 2%) were evaluated in the described LAMP amplification assay (see Example 12). FIG. 18A shows initial testing of four different detergents after inoculating an HSV-1 isolate into the TS containing 2% detergent followed by immediate amplification. FIG. 18B shows comparison of the LAMP amplifications after inoculating the HSV-1 isolate into the TS containing 2% detergent and storing for 2 days at room temperature before amplification to evaluate stability of the viral DNA with each detergent.

DETAILED DESCRIPTION

Unless otherwise defined, technical and scientific terms used in the present teachings described herein shall have the meanings that are commonly understood by those of ordinary skill in the art. Further, unless otherwise required by context, plural terms shall include the singular and singular terms shall include pluralities. Generally, nomenclatures utilized in connection with molecular biology, cell and tissue culture, protein and oligo- or polynucleotide chemistry described herein are well-known and commonly used in the art. Standard techniques are used, for example, for recombinant nucleic acid and protein preparation, purification and analysis, for oligonucleotide synthesis. Purification techniques and enzymatic reactions are performed according to manufacturer's specifications or as described herein or as commonly accomplished in the art. The techniques and procedures described herein are generally performed according to conventional methods well known in the art and as described in various general references that are cited and discussed throughout the instant specification. See, e.g., Sambrook et al., Molecular Cloning: A Laboratory Manual (Third ed., Cold Spring Harbor Laboratory Press, Cold Spring Harbor, N.Y. 2000). The nomenclatures utilized in connection with, and the laboratory procedures and techniques described herein are those well-known and commonly used in the art.

Figure 1:
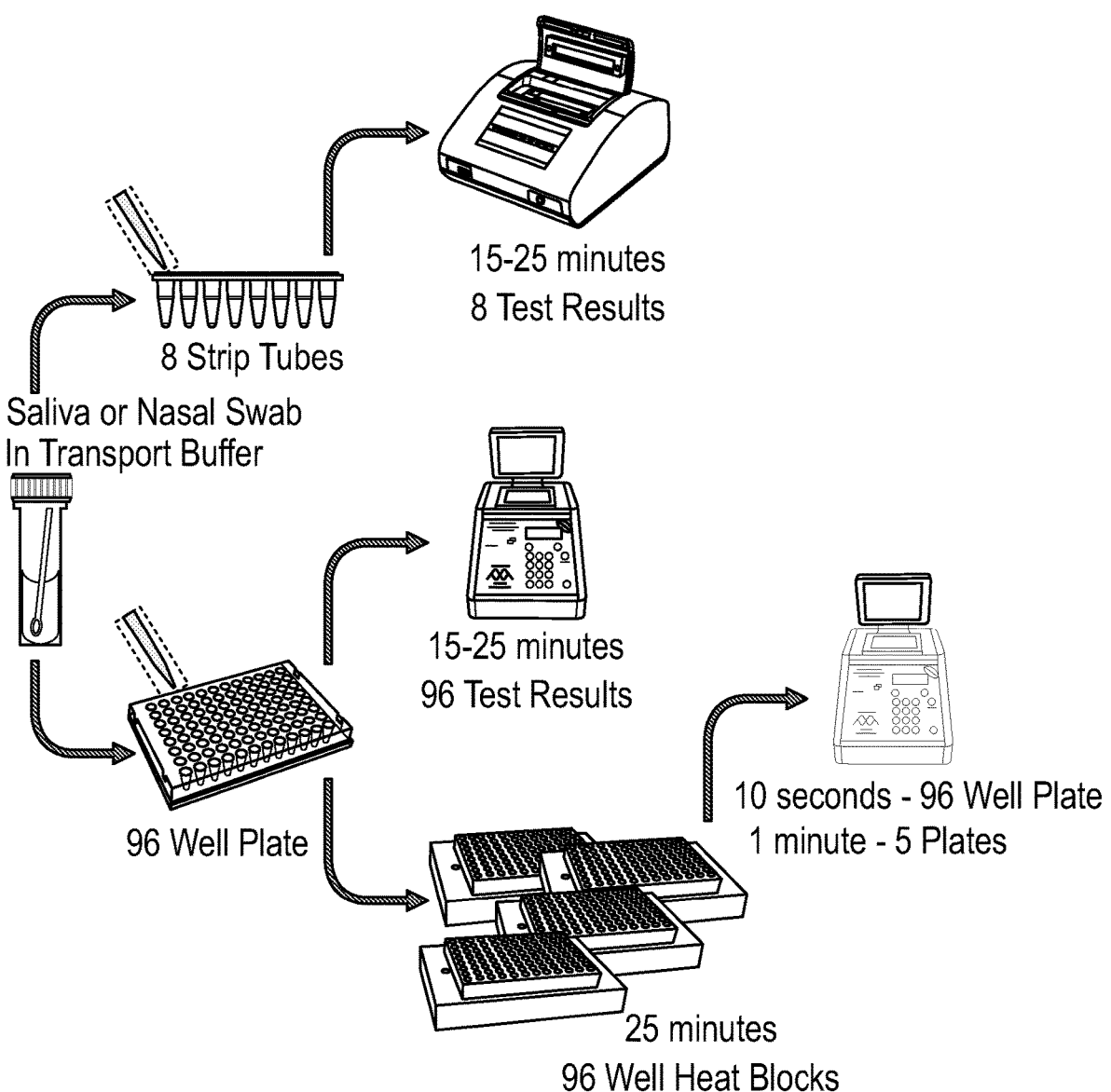
FIG. 1. An example of Point-of-Care Test for an enveloped virus (such as SARS-CoV-2 virus). The method allows for processing hundreds of tests to answer in about 30 minutes. Eliminates nucleic acid extraction step, so no extraction reagents are needed. Maximum number of tests is based on number of Heat Blocks available.

The present invention is directed to novel reagents and methods for rapid detection of pathogens in biological samples. In accordance with one aspect of the invention, the Transport Solution (TS) for a pathogen is provided that serves to inactivate and lyse pathogens as well as preserve the nucleic acids (DNA and/or RNA) of the pathogens at room temperature storage for 4 weeks or longer. The Amplification Solution, optionally containing primers that target a portion of the pathogen genome, can be directly inoculated with the TS containing the lysed pathogen. Isothermal amplification can be performed and a positive/negative answer is reported in 15-30 minutes. A small isothermal instrument can be used in a clinic setting for small numbers of samples. For larger sample numbers (approaching 100), a small footprint real-time PCR instrument can be used. For bulk screening in a rapid fashion, isothermal amplification can be performed in multiple heat blocks followed by end-point reading in a fluorescent reader (FIG. 1). Alternatively, detection via lateral flow (i.e., nucleic acid lateral flow or NALF) can be employed, for example, as disclosed in US 20180023121 A1. Alternatively, a biosensor for detection of amplified nucleic acid molecules can be employed. Various biosensor are known in the field, for example, disclosed in the U.S. Pat. Nos. 8,703,445 B2, 10,620,200 B2, 7,169,358 B2.

The first component of the reagent kit proposed herein for amplifying nucleic acid molecules is the disclosed transport solution, which does not require cold storage and frees up refrigeration space. In addition, it allows resampling of the clinical specimens whereas many other rapid tests (e.g., Alethia, ID Now) use the entire clinical specimen. Resampling is important to confirm diagnosis or test for other suspected pathogens. Nucleic acids (RNA and DNA) are stabilized for extended periods of time (four weeks and more) at room temperature, and are compatible with downstream detection methods. Importantly, the TS inactivates viruses and other pathogens providing safer transport of biospecimens at non-refrigerated temperatures; samples can be processed in non-BSL POC settings.

Another component of the proposed reagent kit for amplifying nucleic acid molecules is an amplification solution, which integrates the transport solution with isothermal amplification, thereby eliminating the need for a separate DNA extraction step. The transport solution is compatible with rapid isothermal amplification tests after extended storage at room temperature, saving valuable time and money. A proposed combination of the transport solution and the amplification solution allows for rapid, CLIA-waived POC testing. Such testing utilizes off the shelf components (e.g., tubes, swabs) and also takes advantage of the standard workflow for clinical specimen collection and processing already familiar to individuals providing direct patient care.

Figure 2:
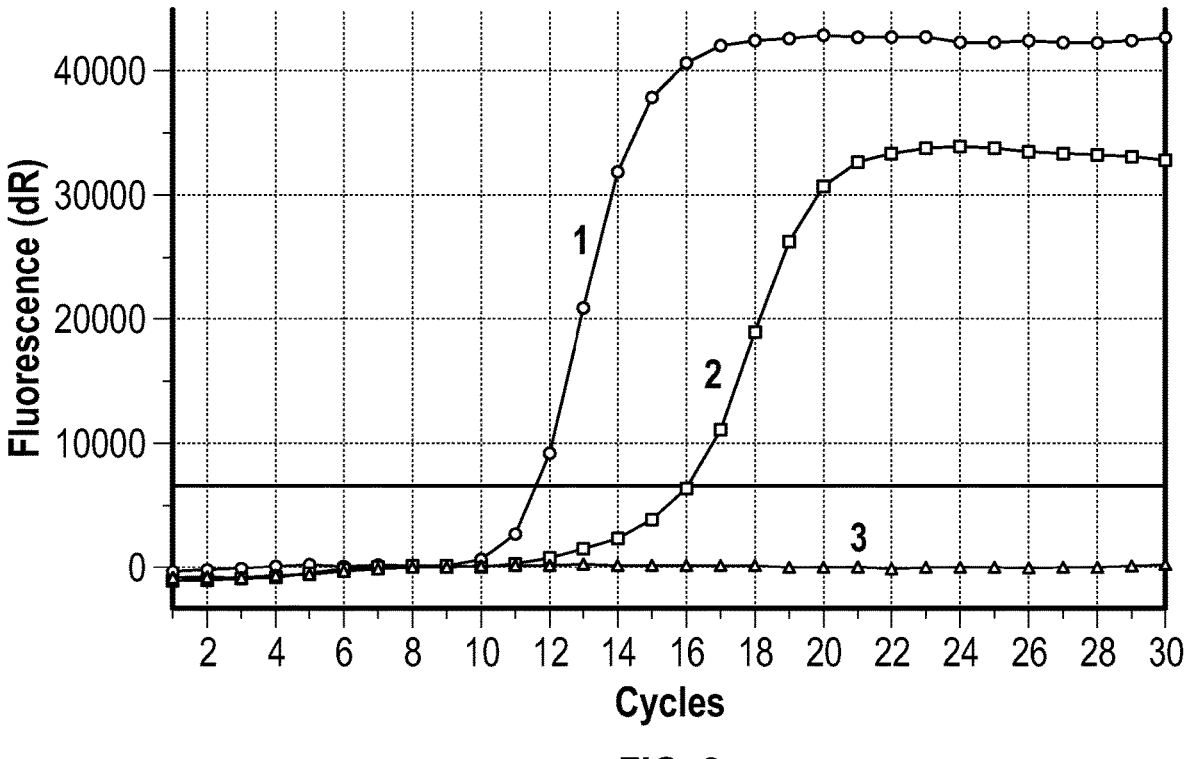
FIG. 2. Exemplary Cytomegalovirus detection. Seven microliters of urine (Reaction 1), positive internal control (Reaction 2; spiked at 25 copies), or buffer (Reaction 3 were pipetted directly into the Amplification Reaction mixture (50 ul reaction volume) and the tube placed into the instrument. Primers are indicated in Table 1. Horizontal bar indicates positive fluorescence threshold. CMV was detected within 12 minutes (Reaction 1) with the CMV test. Aliquots of the urine and buffer were also placed into the TS2 instrument; results also showed positive for CMV as well as the internal positive control and negative for the buffer.
Figure 3:
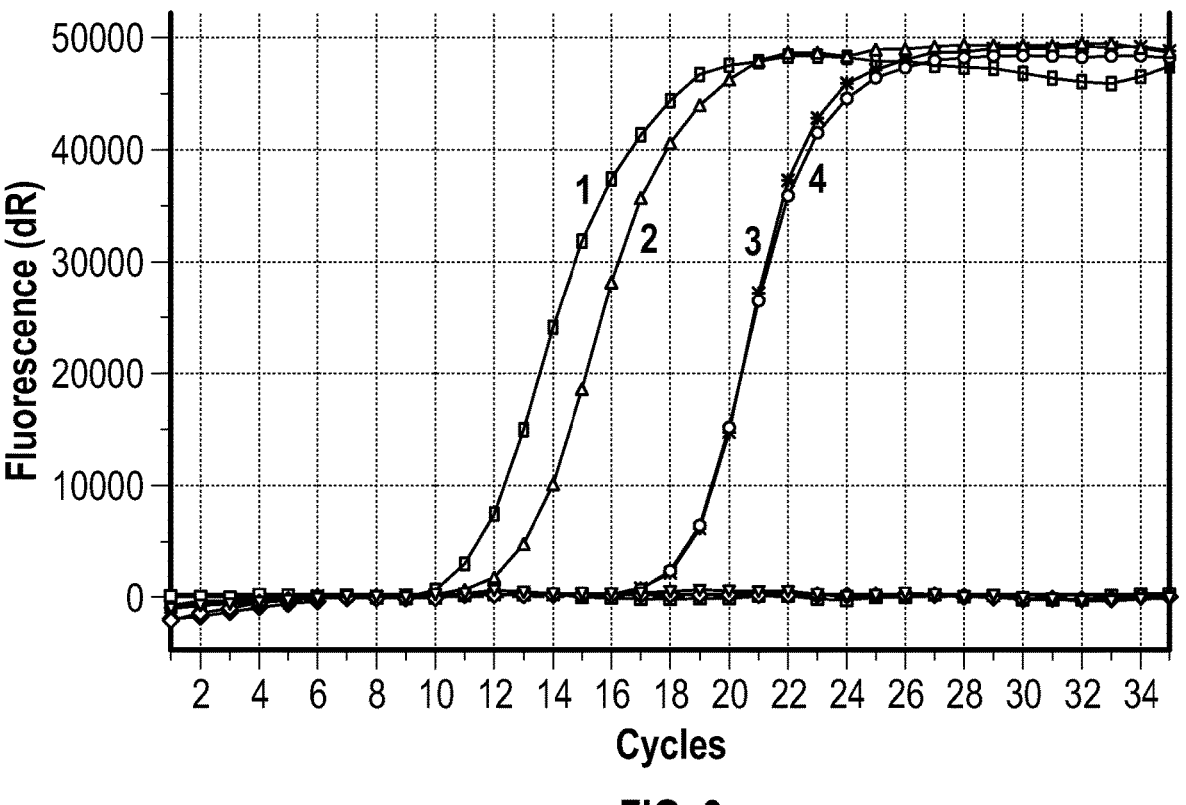
FIG. 3. RT-/LAMP amplification of an IDT gBlock N gene cDNA control and actual specimen from a COVID-19 patient at Baylor Medical Center using primers targeting the N gene in the Amplification Solution. Reactions 1 and 2—IDT cDNA control in duplicate. Reactions 3 and 4—Detection of CoV-2 in a patient sample (nasal swab in 3 mL of viral transport media (VTM)) in duplicate. Each cycle=1 min. Primers are indicated in Table 1.
Figure 4:
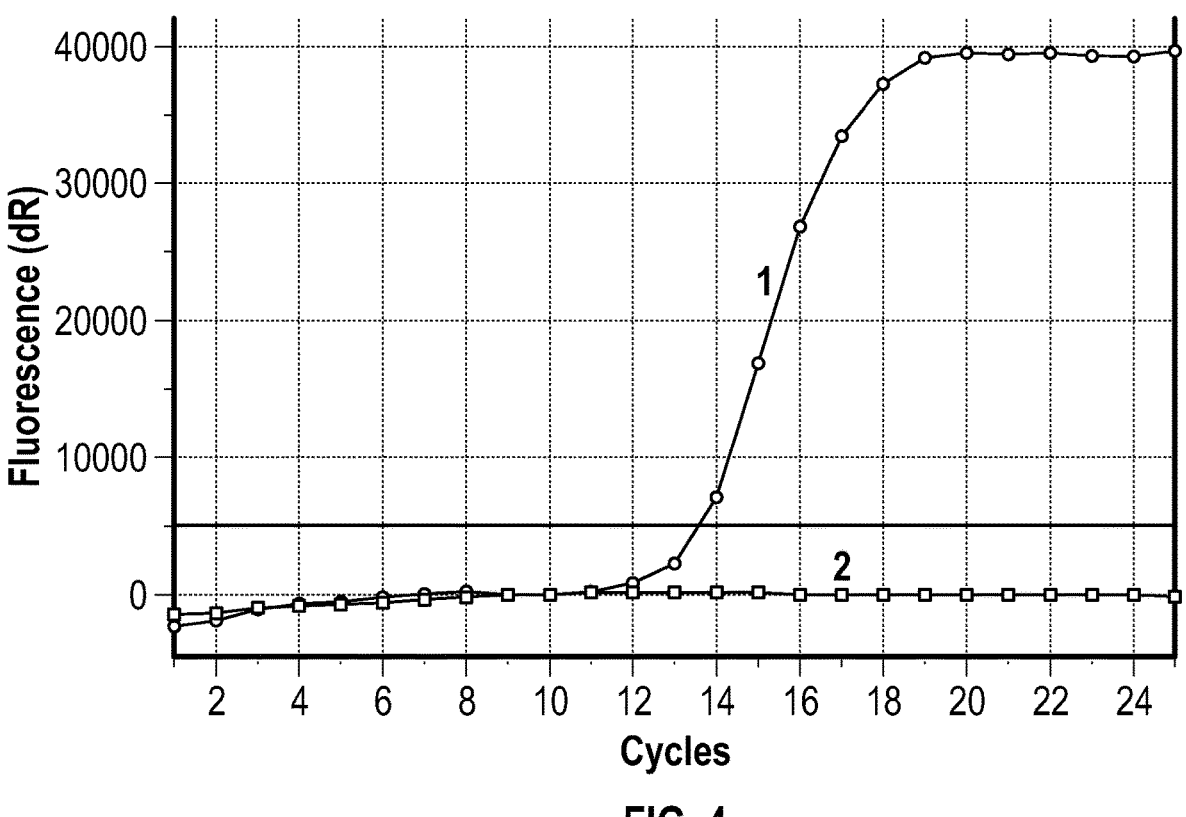
FIG. 4. LAMP amplification of Candida albicans (ATCC 10231; Reaction 1) obtained from a swab in TS containing 2% Triton X-100; positive results were obtained in 14 minutes. Horizontal bar indicates positive fluorescence threshold (5000 RFU) using Eva green. The negative control did not amplify (Reaction 2). Primers are indicated in Table 1.
Figure 5:
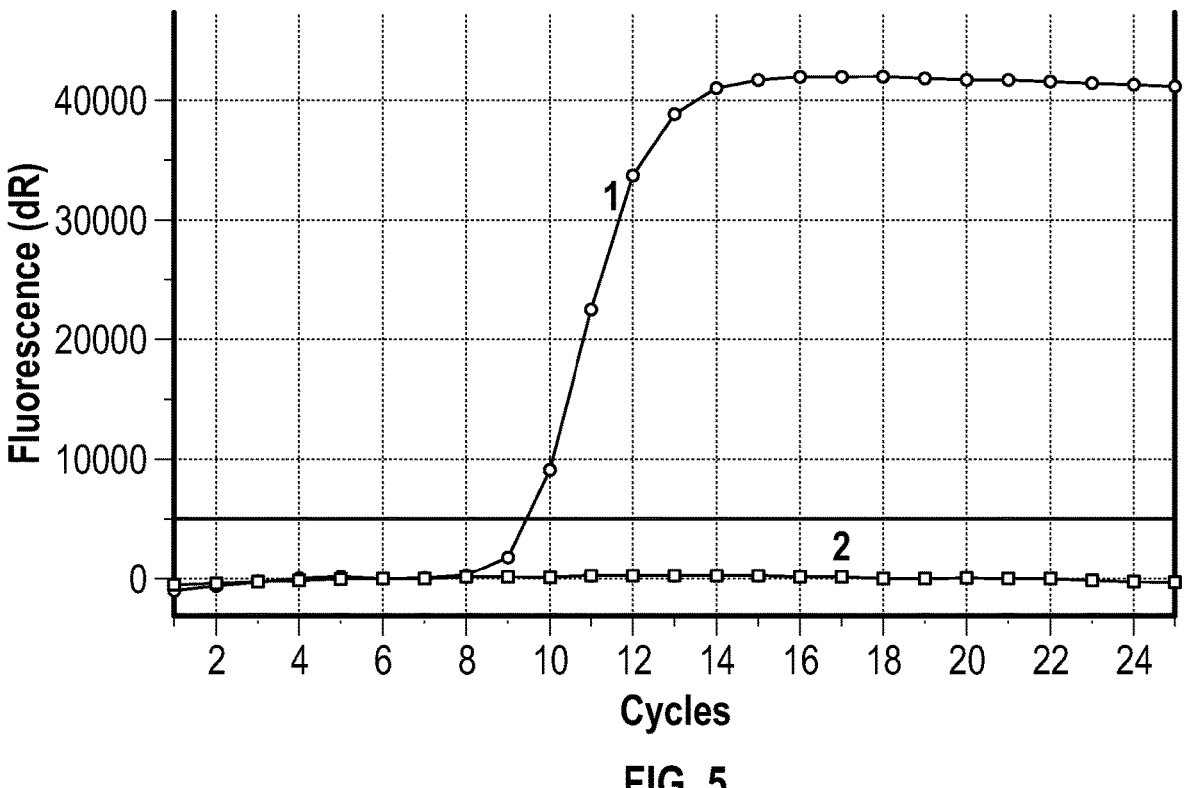
FIG. 5. LAMP amplification of *Chlamydia trachomatis* mucous matrix in TS containing 2% Triton X-100 using the Ct LAMP primers with the Amplification Solution components (Reaction 1). Horizontal bar indicates positive fluorescence threshold (5000 RFU) identified using Eva green. The negative control did not amplify (Reaction 2). Primers are indicated in Table 1.
Figure 6:
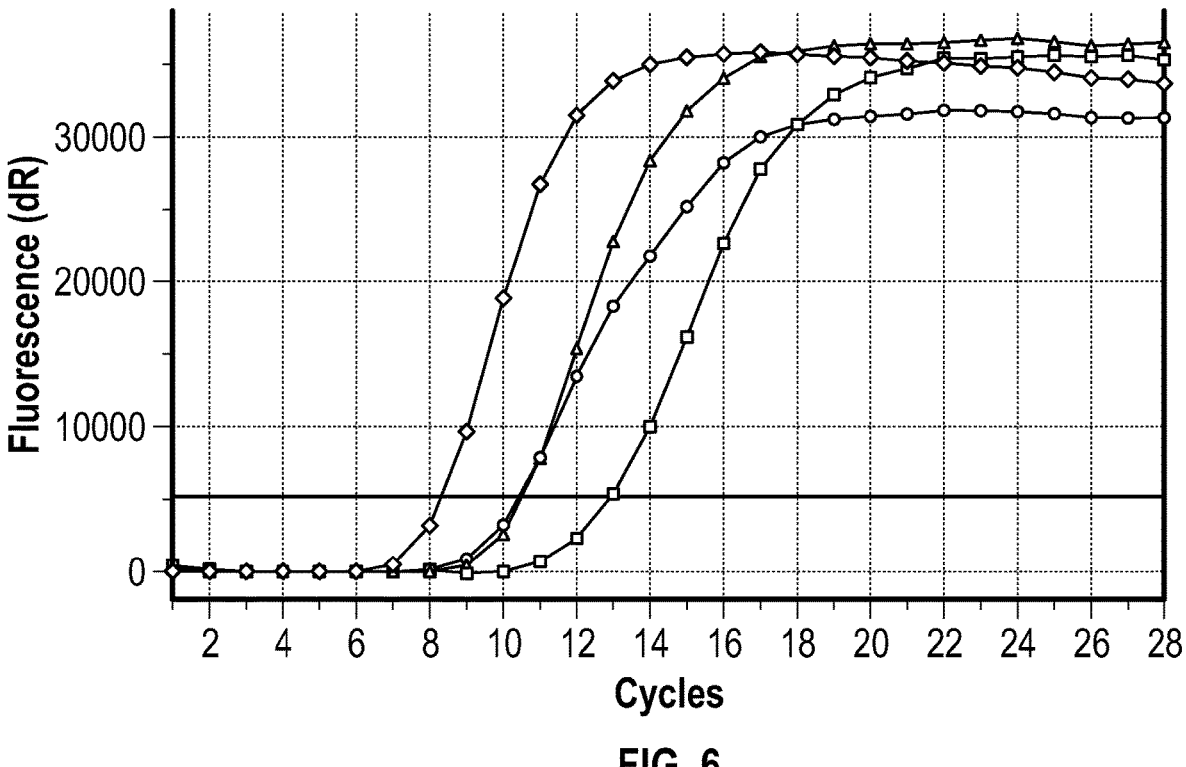
FIG. 6. Stability of 4 HSV-1 clinical samples in the TS containing 2% Triton X-100. Four clinical HSV-1 samples inoculated into the TS containing essentially 2% Triton X-100. Initial inoculation on Jun. 27, 2020 showed all samples had DNA amplifiable by LAMP isothermal amplification (data not shown). The samples were kept at room temperature for 39 days. An equal volume (25 ul) of HSV-1 inoculated TS was incubated with the Amplification Solution (25 ul). Results of the LAMP isothermal amplification show that HSV-1 DNA is still amplifiable after 39 days using TS.
Figure 7:
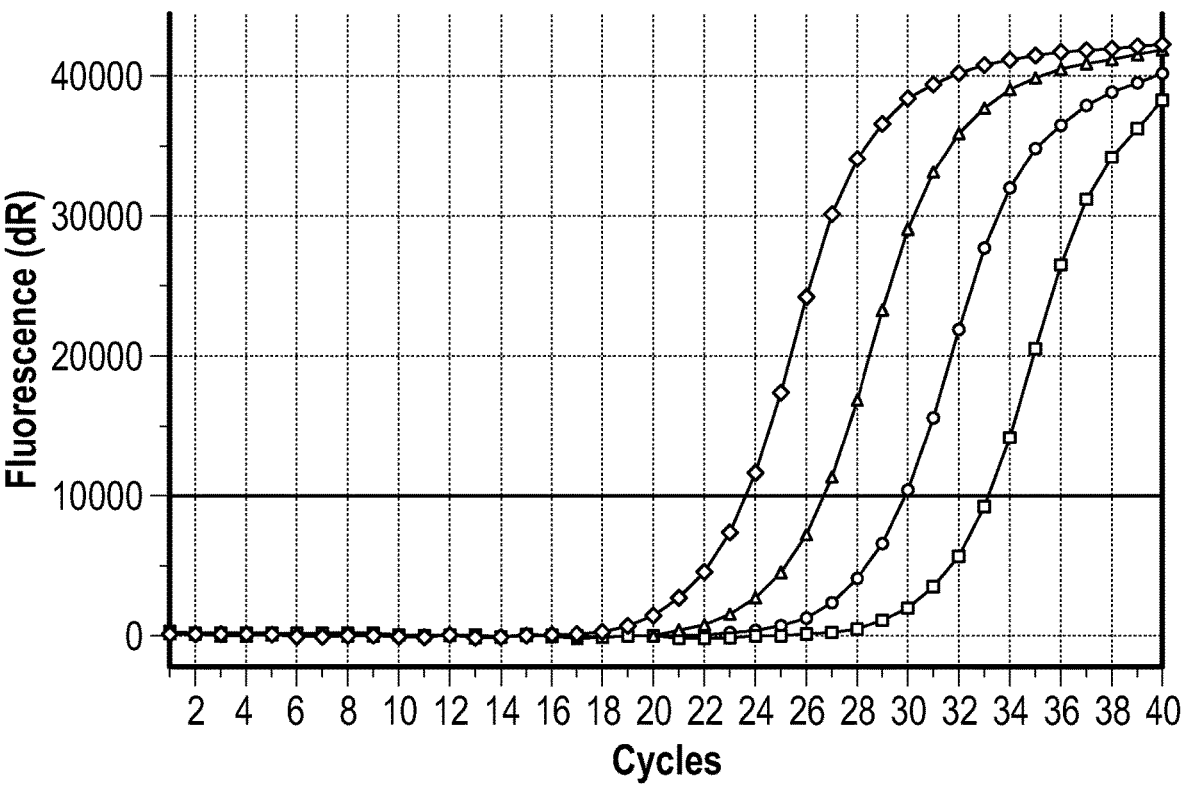
FIG. 7. PCR test of 4 HSV-1 samples. Four clinical HSV-1 samples inoculated into the TS containing essentially 2% Triton X-100. Initial inoculation on Jun. 27, 2020 in which all samples had DNA amplifiable by LAMP isothermal amplification. Samples were kept at room temperature for 39 days. Five microliters of inoculated TS were directly added to the PCR reaction mix (25 ul total reaction volume; NEBs 2× Phusion master mix). Results of the LAMP isothermal amplification show that HSV-1 DNA is still amplifiable after 39 days via PCR.
Figure 8A:
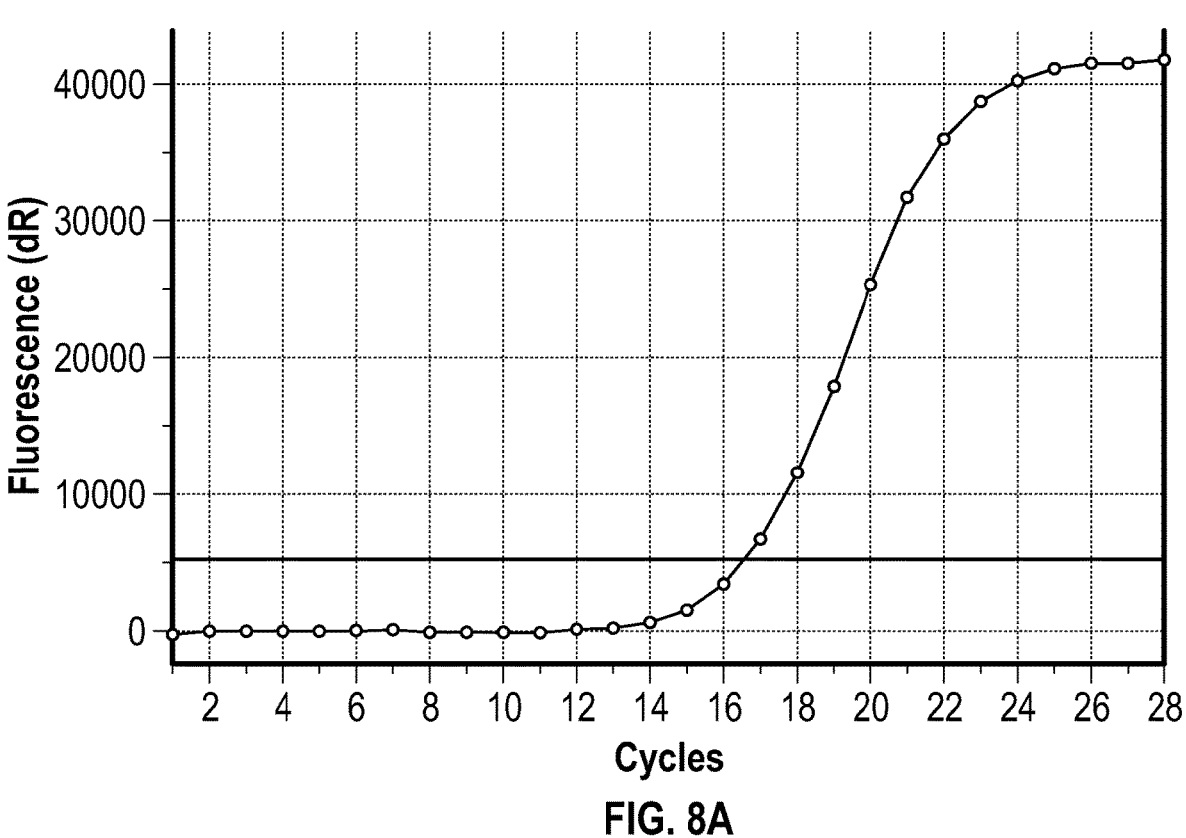
FIG. 8. RNA from SARS-CoV-2 strain USA WA1/2020 was inoculated into the TS containing 2% Triton X-100. Initial inoculation was Jul. 7, 2020 in which all samples were amplifiable by isothermal amplification (data not shown). Samples in the TS were kept at room temperature. Results (FIG. 8A) show CoV-2 RNA was still amplifiable after 29 days in the TS. On day 29, 5 ul of the TS containing pathogen RNA were taken and reverse transcribed into cDNA and evaluated for PCR quality using the CDC N1 primer set. Five microliters of the cDNA were directly added to the PCR reaction mix (25 ul total reaction volume; NEBs 2× Phusion master mix). Results (FIG. 8B) show that RNA was amplifiable by RT-PCR even after 29 days at room temperature in the TS.
Figure 8B:
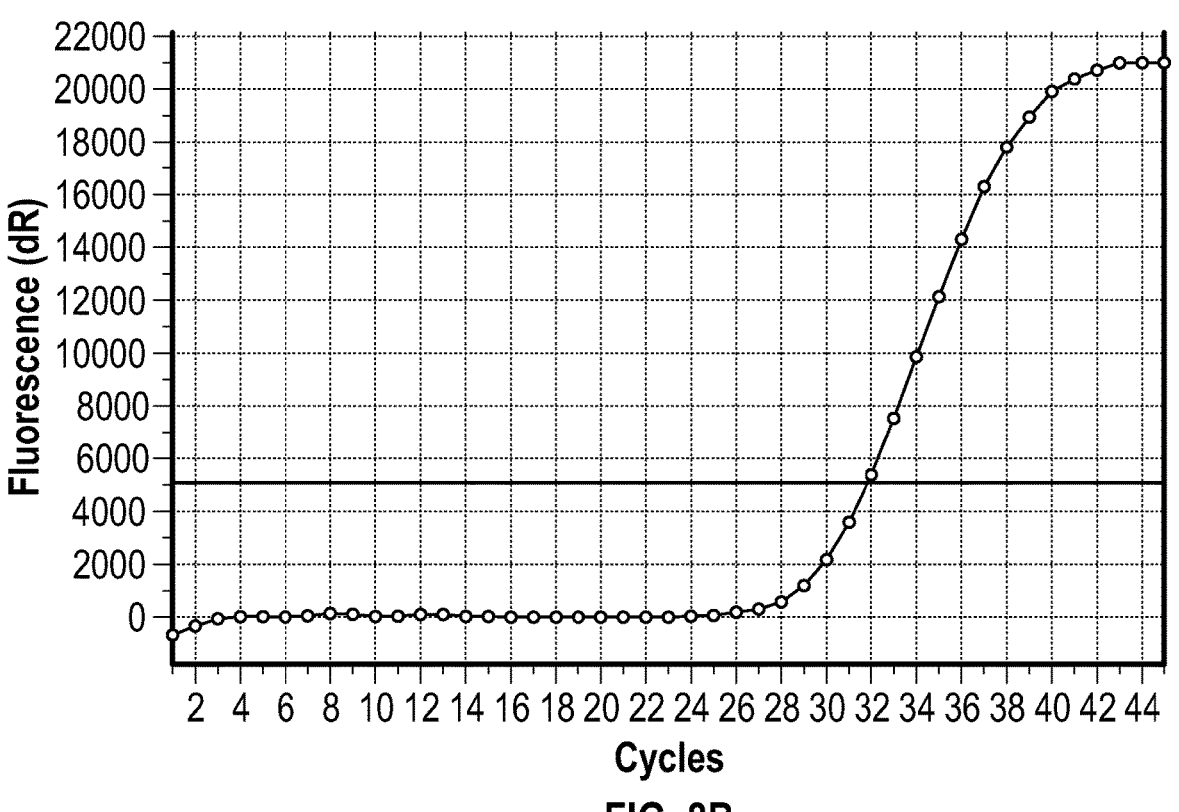
Figure 13:
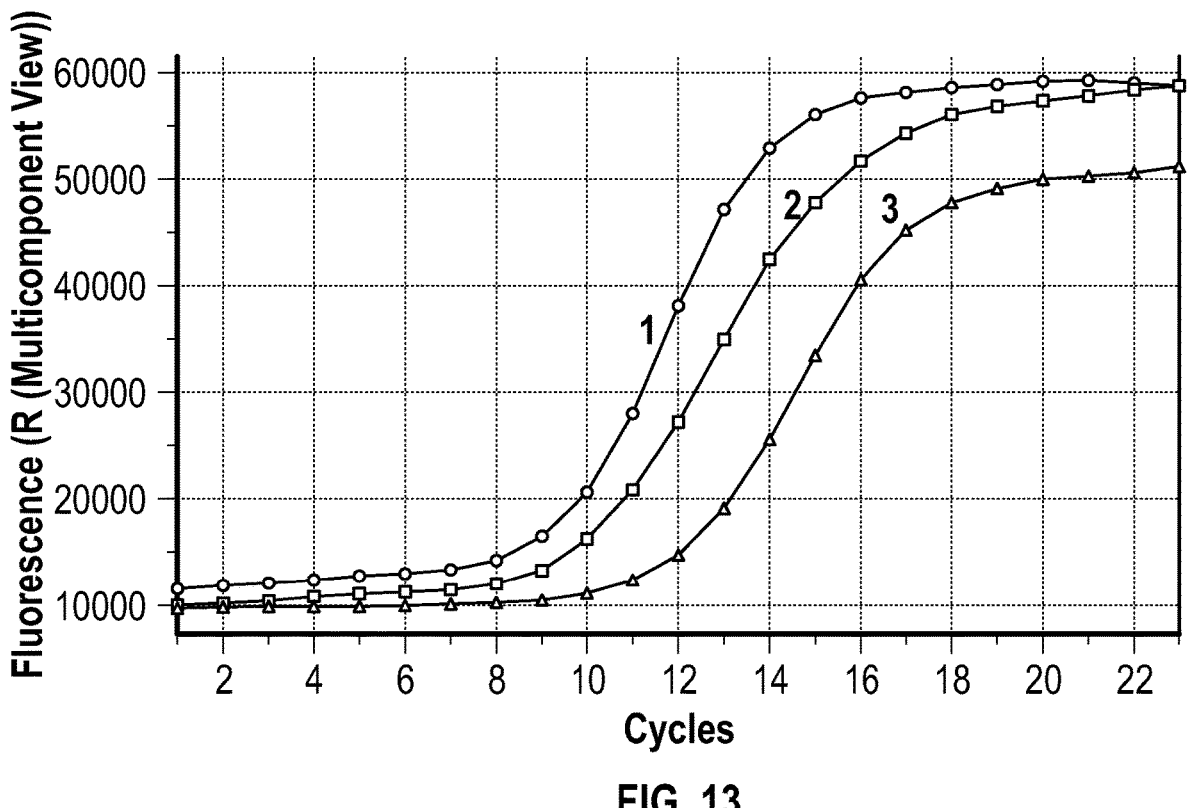
FIG. 13. Increasing the LAMP assay efficiency by adjusting Triton X-100 concentration in the amplification mixture. The LAMP assay reactions for EBV detection were carried out with a standard Amplification Solution and have varying final concentrations of Triton X-100 in the amplification reaction mixture: Reaction 1-1% of Triton X-100, Reaction 2-4% of Triton X-100; Reaction 3-16% of Triton X-100.
Figure 14:
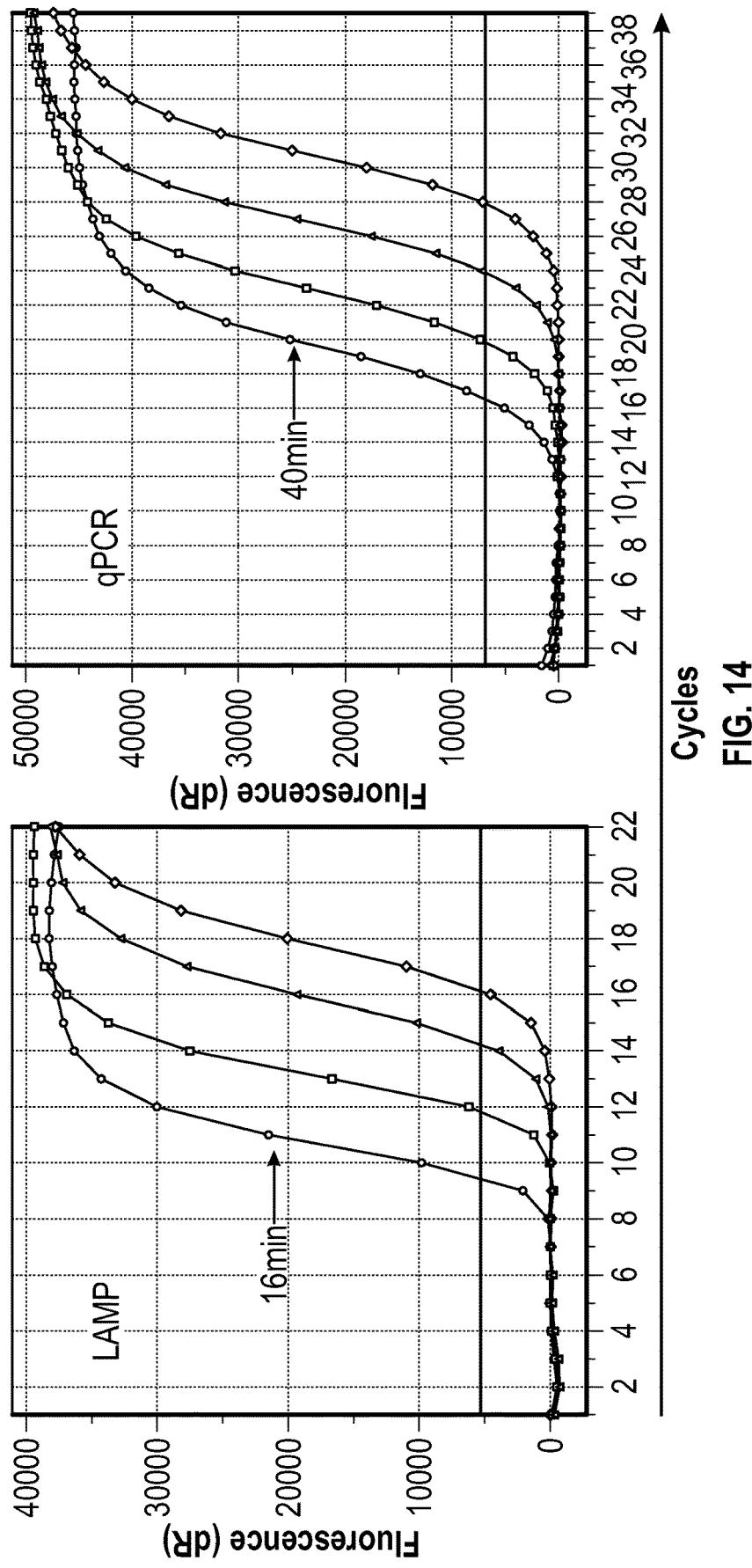
FIG. 14. Comparison of EBV DNA (HR1) amplification using LAMP and qPCR. The LAMP and qPCR methods were compared using the same dilutions of EBV DNA and the same fluorescent reporter (EvaGreen dye) measured in an MX3005P real-time PCR instrument.
Figure 15:
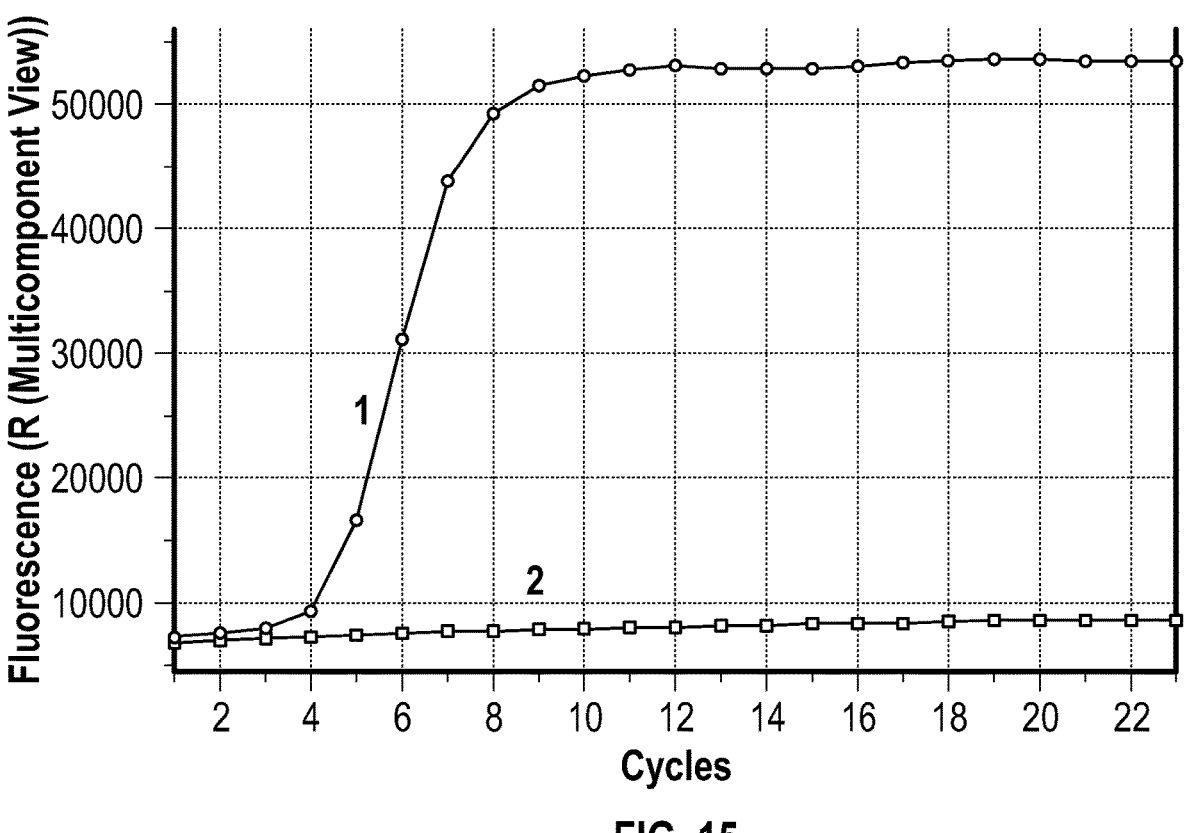
FIG. 15. Detection of Human herpesvirus-8 or Kaposi's sarcoma virus (KSHV). The LAMP assay reactions were carried out to amplify the ORF73 gene of HHV-8 for detection of KSHV. Pathogen was obtained from a swab in the TS. Reaction 1—HHV-8 containing sample; Reaction 2—negative control.

The proposed identification test system and reagent kit are applicable to multiple pathogen types such as viruses, in particular, enveloped viruses, bacteria, and fungi, such as yeast. Examples of the performance of the test system with real patient samples or spike matrices for Cytomegalovirus (FIG. 2), SARS-CoV-2 (FIG. 3, FIG. 8), Candida albicans (FIG. 4), *Chlamydia trachomatis* (FIG. 5), HSV-1 (FIGS. 6, 7, 11), CMV (FIGS. 9, 10, 12), EBV (FIGS. 13, 14) and KHSV (FIG. 15) are presented herein. The exemplary primer sets used to perform these experiments, as well as the experiments in other examples are disclosed in the following Table 1.

TABLE 1

Pathogen Primer sets. Dashes ("-") indicate places where a set of TTTT may be added.

| SEQ ID NO: | Pathogen | Name | Primer sequence |
|---|---|---|---|
| 1 | CMV | FIP | CGATAACCACCGAACCCGCAATTTTTCCTTTCCCTCGGCTTCTCA |
| 2 | | BIP | CATGTACCCCGTATGCATGGCCTTTTGTAAAGCTCGGCCATAGTGT |
| 3 | | LF | GTGCTGGCCGGATTGTTG |
| 4 | | LB | AAGACTAACTCGCCCAACTATAAGC |
| 5 | SARS-CoV-2 | FIP | CCACTGCGTTCTCCATTCTGGTTTTTAAATGCACCCCGCATTACG |
| 6 | | BIP | CGCGATCAAAACAACGTCGGCTTTTCCTTGCCATGTTGAGTGAGA |
| 7 | | LF | CAGTTGAATCTGAGGGTCCACCAAA |

TABLE 1-continued

Pathogen Primer sets. Dashes ("-") indicate places where a set of TTTT may be added.

| SEQ ID NO: | Pathogen | Name | Primer sequence |
|---|---|---|---|
| 8 | | LB | TTACCCAATAATACTGCGTCTTGG |
| 9 | EBV BALF 5 | FIP | TCCCATCCCAACAGTGTGTGTCTTTTGATCCGACACCCGTGCTT |
| 10 | | BIP | GGTGATCTTGTGGTAGTCGCCGTTTTCGGGTCTCGGTGGAGAAG |
| 11 | | LF | GCCACGTGGCTGCAAGA |
| 12 | | LB | GCATGGTTGCCGTAGCC |
| 13 | EBV IR | FIP | AGCTGTCCGAGGGGACCCTTTTTCACCACACCCAGGCACAC |
| 14 | | BIP | GTCCTACCAGAGGGGGCCATTTTCCGCTTACCACCTCCTCTTC |
| 15 | | LF | CGGGTGGGTGTGTGTAGT |
| 16 | | LB | AGAACCCAGACGAGTCCGTA |
| 17 | HSV-1 | FIP | GTTTTTGCCGCCCATCAGGCTGTTTTGCATGGCCGGCAACGA |
| 18 | | BIP | CCTTATTTTTGACCGCACCCGCTTTTAGGCCGCGCACACAA |
| 19 | | LF | TCCCGGCCTGAAACACAC |
| 20 | | LB | AAGTTCGTCCTGGCCTGTCC |
| 21 | HSV-2 | FIP | GTAGTCCCGGTCCGCCTCCATTTTTCCAGGCCCACAACCT |
| 22 | | BIP | TGGAGATCGAGGTGGGGGGTTTTGCAGCAGGATGCTCAGCA |
| 23 | | LF | GGGAGAGCGTACTGAAGCAC |
| 24 | | LB | CTGTTCTTCGTGAAGGCCCAC |
| 25 | VZV | FIP | AGGGCCCCGTGTAACATATCCATTTTTTGTAGGCCTTGCAAGTGC |
| 26 | | BIP | TCACGGCCTGTTATTTCCTCGGTTTTAGGGTCCAAAACCACTGC |
| 27 | | LF | CTCTTTTTTTCTTGGCGTTGGTAC |
| 28 | | LB | ATGCCACCAAACAGTAAATCCC |
| 29 | Chlamydia tri. | FIP | TCGAGCAACCGCTGTGACGACCTTCATTATGTCGGAGTC |
| 30 | | BIP | GCAGCTTGTAGTCCTGCTTGAGTCTTCGTAACTCGCTCC |
| 31 | | LF | TACAAACGCCTAGGGTGC |
| 32 | | LB | CGGGCGATTTGCCTTAAC |
| 33 | Candida alb. | FIP | AACGACGCTCAAACAGGCATTTTTCGTGAATCATCGAATCTTTGAAC |
| 34 | | BIP | CTGGGTTTGGTGTTGAGCAATTTTATCCCGCCTTACCACTAC |
| 35 | | LF | ACCAGAGGGCGCAATGTG |
| 36 | | LB | ACGACTTGGGTTTGCTTGAAAGA |
| 37 | HHV-8 | FIP | TCGCTGGATGATCCCACGTAGATTTTTGTGACTTCGCCAACCGTA |

US 12,680,126 B2

13                                                                14

TABLE 1-continued

Pathogen Primer sets. Dashes ("-") indicate places where a set of TTTT
may be added.

| SEQ ID NO: | Pathogen | Name | Primer sequence |
|---|---|---|---|
| 38 | | BIP | CGATACTCCGCCACGCCAACTTTTACCCCAGGATCCCTCAGA |
| 39 | | LF | GGGACTCTGTGGCCCAT |
| 40 | | LB | CGCCTACATCTCCCATCTCC |

In one embodiment of the invention, TS comprises a non-ionic or zwitterionic detergent at a concentration of 2 to 32 percent (vol./vol.). In another embodiment, TS further comprises a buffering agent that has a pH between about 5 and about 11, and a chelating agent. In yet another embodiment, TS consists essentially of the non-ionic or zwitterionic detergent at a concentration of 1 to 32 percent (vol./vol.), and a swab (oral, nasal, lesion, etc.) is placed into a tube containing the detergent. The non-ionic or zwitterionic detergent can be selected from Triton X-100, NP-40, Tween 20, Tween 80, CHAPS, CHAPSO. In another embodiment of the invention, TS consists essentially of a non-ionic detergent at a concentration of 2 to 10 percent (vol./vol.). In yet another embodiment of the invention, TS consists essentially of a zwitterionic detergent at a concentration of 2 to 10 percent (vol./vol.).

The maximum concentration of a non-ionic or zwitterionic detergent in amplification reaction mixture should be 16% (v/v) or less, since concentrations higher than 16% (v/v) significantly inhibit amplification reactions. A combination of non-ionic and/or zwitterionic detergents can be used when the total concentration (the sum of independent concentrations) is below 16% (v/v). Preferably, the overall concentration of non-ionic and/or zwitterionic detergent(s) in the lysis mixture is ≤15%, preferably ≤10% (v/v), more preferably ≤5% (v/v). Preferably, Tween-20, Nonidet P-40 (or Triton X-100) or CHAPS, or a mixture thereof, is used. The concentration of $MgSO_4$ in the amplification reaction mixture is preferably less than 3 mM (v/v), preferably in a range from 0.5 mM (v/v) to 2 mM (v/v), more preferably in a range from 1 mM (v/v) to 2 mM (v/v). The concentration of serum albumin (bovine or human) in the amplification reaction mixture is preferably in a range from 100 µM to 500 µM, more preferably in a range from 200 µM to 400 µM.

In some embodiments of the invention, a final concentration of a non-ionic or zwitterionic detergent in amplification reaction mixture is between 1% (v/v) and 2% (v/v). In other embodiments of the invention, a final concentration of a non-ionic or zwitterionic detergent in amplification reaction mixture is between 2% (v/v) and 5% (v/v). In yet other embodiments of the invention, a final concentration of a non-ionic or zwitterionic detergent in amplification reaction mixture is between 5% (v/v) and 10% (v/v). Lower concentration of non-ionic or zwitterionic detergent in amplification reaction mixture usually would result in a higher amplification efficiency; however, at the same time, higher concentration of the non-ionic or zwitterionic detergent in the Transport solution (TS) would help with complete pathogen inactivation. Based on the provided Examples below, different concentration ranges from 1 to 16% of Triton X-100 or similar non-ionic detergent, such as NP-40 or Tween-20, can be utilized in the amplification mixture for different pathogens and different assays. Concentration of Triton X-100 or similar non-ionic detergent, such as NP-40 or Tween-20, in Transport Solution (TS) can be formulated accordingly (typically, twice higher than in the amplification mixture). Typically, concentrations of detergent equal or higher than 2% (v/v) in the TS are sufficient for pathogen inactivation (see e.g. Jonges M, et al., Influenza virus inactivation for studies of antigenicity and phenotypic neuraminidase inhibitor resistance profiling. J Clin Microbiol. 2010 March; 48(3):928-40; Remy M M, et al., Effective chemical virus inactivation of patient serum compatible with accurate serodiagnosis of infections. Clin Microbiol Infect. 2019 July; 25(7):907. e7-907. e12; Rabe B A, Cepko C. SARS-CoV-2 detection using isothermal amplification and a rapid, inexpensive protocol for sample inactivation and purification. Proc Natl Acad Sci USA. 2020 Sep. 29; 117 (39):24450-24458). Mechanism of action behind inactivation of pathogens (including enveloped viruses and bacteria) with a high concentration of Triton X-100 or similar non-ionic detergent is known and relates to formation of micelles at critical micelle concentration of the detergent, followed by denaturation of pathogen's structure.

Sequence-specific isothermal nucleic acid amplification techniques represent a growing sector of molecular diagnostics, offering rapid, sensitive detection without the need for thermal cycling equipment as required for the PCR. Several isothermal nucleic acid amplification protocols have been developed, including transcription-mediated amplification or self-sustained sequence replication, nucleic acid sequence-based amplification, signal-mediated amplification of RNA, strand displacement amplification, rolling circle amplification, loop-mediated isothermal amplification of DNA, isothermal multiple displacement amplification, helicase-dependent amplification, single-primer isothermal amplification, and circular helicase-dependent amplification. In contrast to PCR, which denatures double-stranded DNA (dsDNA) with heat, isothermal amplification techniques typically use enzymatic activity to provide strand separation of dsDNA. Furthermore, isothermal techniques typically provide comparable or better detection limits compared with PCR but in a fraction of the reaction time. These methods have particular interest to POC molecular diagnostics due to advantages in efficiency, cost, and instrumentation.

Loop-mediated isothermal amplification (LAMP) is potentially one of the best options for the development of point-of-care devices. LAMP of genomic sequence is a novel method for the detection of nucleic acid with high specificity and sensitivity without the need for specialized equipment. The principle of LAMP is based on autocycling strand displacement DNA synthesis in the presence of exonuclease-negative Bst DNA polymerase under isothermal condition within one hour (Notomi, 2000). The use of four designed primers allows highly specific detection of six distinct sequences in the target DNA. Inner primers, designated "forward inner primers" (FIP) and "backward inner primers" (BIP), are designed to detect two regions each. Forward and reverse outer primers, F3 and B3, detect a single region each. Two additional "loop" primers can be added to increase reaction speed, resulting in six total primers used per target sequence. The products are stem-loop DNA structures with several inverted repeats of target and cauliflower-like structures with multiple loops. The LAMP reaction rapidly (completed in as little as 5 min) generates amplification products as multimers of the target region in various sizes and is substantial in total DNA synthesis (>10 µg, >50×PCR yield). Possible variations in LAMP format are known in the field and disclosed, for example, in U.S. Pat. No. 10,724,079B2, US20180135108A1, U.S. Pat. Nos. 9,469,870B2, 10,450, 616B1, US20190218604A1, the contents of which are incorporated herein.

Other methods of isothermal amplification, such as strand displacement amplification (SDA), rolling circle amplification (RCA), recombinase polymerase amplification (RPA), and Helicase dependent Isothermal DNA Amplification (HAD) have been reported to be utilized for amplifying nucleic acids and subsequent pathogen detection.

LAMP reactions allow amplification of templates at a target temperature of between 60 to 67° C., utilizing a polymerase enzyme with strong strand displacement and replicative activities amplifying two to three sets of DNA primers. LAMP generally employs at least four primers targeted precisely to targeting six distinct regions on the gene to maximize specificity. The high degree of amplification of a target DNA (or RNA, with transcription/replication enabled enzymes) achieved due to the high target specificity allows detectable signal to be produced via fluorescent or colorimetric dyes that intercalate or directly label DNA, allowing a correlation with the initial copy number and therefore quantitative measurement.

When compared to PCR, LAMP is more sensitive, so that it can amplify a negligible amount of DNA to 100s copies within 30 minutes. LAMP requires an enzyme which has a DNA polymerizing capacity along with an enhanced ability to displace the DNA strand. Suitable enzymes are, for example, Bst polymerase isolated from *Bacillus stearothermophilus* and Bsm polymerase isolated from *Bacillus smithii*. Both enzymes have an enhanced property of strand displacement and can catalyze 5'-3' DNA polymerization but they don't have 5'-3' exonuclease activity. The optimized versions of Bst polymerase are commercially available, for example, Bst 2.0 or Bst 3.0 DNA polymerases. Specificity and overall performance of LAMP mainly relies on designing specific primers. In some embodiments, in addition to F3 (Forward outer), B3 (Backward outer), FIP (Forward inner) and BIP (Backward inner) primers, two more primers, LF (Loop forward) and LB (Loop backward), may be incorporated which can further accelerates the reaction. In some embodiments, F3 and B3 primers are not required for LAMP and only FIP, BIP, LF and LB primers are required. The sequence requirements for optimal LAMP primers are known for specialists in the art and may include some of the following: GC content should be about 50-60%; inner primers should not have AT rich sequence at both the ends; primers should not form any secondary loop structures. There are a few publicly available programs that can help with designing primer sequences, for example, Primer Explorer (https://primerexplorer.jp/e/). LAMP primers can be designed based on alignments of published pathogen coat protein sequences. For multiplex LAMP, primers can be designed to optimize discrimination between two or more pathogens. Degenerate bases can be incorporated into primers to mitigate against intraspecific variations.

Detection of the LAMP amplified products can be achieved via a variety of methods, including colorimetric detection using fluorescent dyes, UV light irradiation, agarose gel electrophoresis, turbidity, real-time fluorescence, lateral flow assay, and smartphone. For example, using a turbidimeter or absorbance-based (650 nm) plate reader, the optical density of LAMP reactions can be monitored for a white precipitation that is caused by the generation of magnesium pyrophosphate, $Mg_2P_2O_7$ (product generated during LAMP). In one embodiment, detection of a product is conducted by adding a fluorescently-labeled probe to the primer mix. The term "probe" refers to a single-stranded nucleic acid molecule comprising a portion or portions that are complementary, or substantially complementary, to a target sequence. In certain implementations, the fluorescently-labeled probe is a molecular beacon. As used herein, "molecular beacon" refers to a single stranded hairpin-shaped oligonucleotide probe designed to report the presence of specific nucleic acids in a solution. A molecular beacon consists of four components; a stem, hairpin loop, end labelled fluorophore and opposite end-labelled quencher. When the hairpin-like beacon is not bound to a target, the fluorophore and quencher lie close together and fluorescence is suppressed. In the presence of a complementary target nucleotide sequence, the stem of the beacon opens to hybridize to the target. This separates the fluorophore and quencher, allowing the fluorophore to fluoresce.

In another embodiment, RT-LAMP assay can be used with a microfluidic chip combined with a pH indicator and a smartphone to detect a virus, similar to disclosed in Kaarj, K. et al., Sensitive Zika Virus Assay Using Smartphone Detection of Loop-mediated Isothermal Amplification on Paper Microfluidic Chips. Sci. Rep. 2018. Using the pH change of productive LAMP reactions, virus-positive samples from urine and human plasma can be quantified with the pH-induced color change after only 15 min using the smartphone camera.

However, similar to PCR, an important limitation of the LAMP technology is that a DNA isolation step is required before amplification. Without this upfront step, there is a high incidence (~40%) of reaction failure (Kaneko, 2005). A separate DNA isolation step adds time, complexity, and the potential for contamination. Furthermore, different DNA extraction methodologies are typically used for different biospecimen types (e.g., saliva vs. urine); thus, each POC test is often approved for one sample type or another but usually not both.

A separate DNA isolation step adds time, complexity, and the potential for contamination. Furthermore, different DNA extraction methodologies are typically used for different biospecimen types (e.g., saliva vs. urine); thus, each POC test is often approved for one sample type or another but usually not both.

Regarding COVID-19, several POC tests are available. The most highlighted is Abbott's ID now COVID-19 test. This is an isothermal test that requires placing the swab into a solution chamber followed by a period of incubation. After this step, the chamber is then placed into a 2nd chamber for testing. The test results are reported within 15 minutes. However, there are significant limitations to the Abbott ID class of tests. First, there are multiple steps involved during the procedure (i.e., user intervention). Second, the workflow effectively dilutes the sample; some investigators have noted that there is up to a 30% false negative rate. Lastly, only one patient sample can be run at a time on each instrument. Most other similar tests also have the same workflow-sample lyse and dilute, transfer to another chamber, and test with results reported 30-45 minutes. Thus, there are significant drawbacks to this type of test and workflow.

Disclosed herein are novel reagent products that can provide a lysis of the pathogen, stabilization of the pathogen's nucleic acid and can further accelerate the isothermal amplification reaction, overcoming the major limitation in current LAMP assays. First, "Transport Solution" (TS) that is compatible with isothermal nucleic acid amplification test is developed as a safe, inexpensive alternative to known viral transport media (VTM). TS likely inactivates enveloped viruses, such as SARS-CoV-2, allowing safe handling and transport of the sample and is compatible with downstream nucleic acid amplification testing. Second, "Amplification Solution" that allows direct addition of the sample (saliva or NP swab directly into TS) to a rapid isothermal assay. It is a simple one-step assay in which 25 ul of inoculated TS is added to the reagent tube containing 25 ul Amplification Solution with target primers; results are reported within 25 min. Preliminary data shows the disclosed TS and Amplification Solution-isothermal POC test works with multiple DNA viruses, bacteria, yeast, and most recently, SARS-CoV-2. The Amplification Solution allows rapid nucleic acid amplification (15-25 min), robust (no separate nucleic acid extraction step), and can be performed on multiple existing instruments (e.g., portable isothermal or 96-well PCR instruments). In addition, to increase the number of samples analyzed the tubes can be placed in a heat block followed by an end-point reading on the instrument. Lastly, TS is directly compatible with RT-PCR methodology thus bypassing the need for RNA or DNA extraction and purification.

Figure 9:
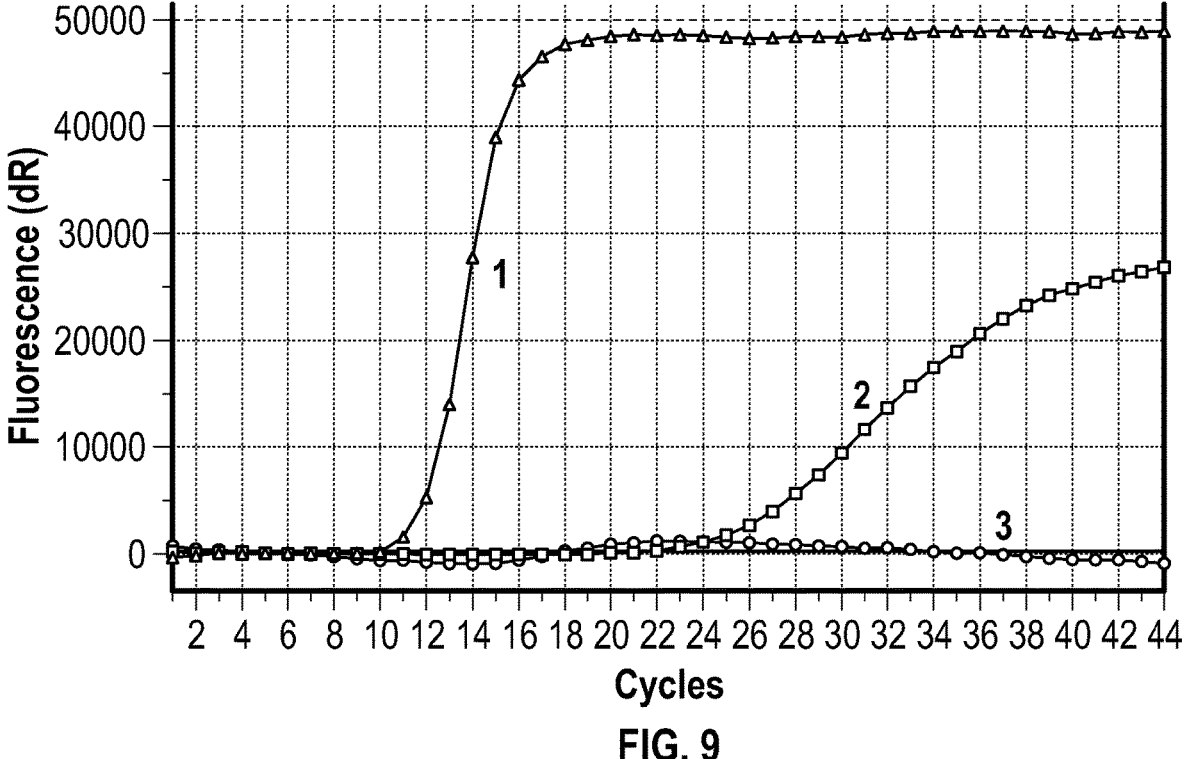
FIG. 9. LAMP amplification of heat-inactivated CMV-spiked urine in TS (2% Triton X-100) using: Reaction 1—CMV LAMP primers with the Amplification Solution components; Reaction 2—CMV LAMP primers with NEB 2× buffer and lysis components; Reaction 3—CMV LAMP primers with NEB 2× buffer only (negative control). Each cycle=1 minute. Horizontal bar indicates positive fluorescence threshold (5000 RFU) using Eva green. Similar results were found for saliva (not shown).

The disclosed combination of TS and Amplification Solution provides an optimized reagent kit capable of inactivating a pathogen via lysing its envelope, stabilizing a pathogen's nucleic acid and further enabling accelerated detection via an isothermal amplification, preferably LAMP, as compared to NEB 2×LAMP buffer. For example, this combination resulted in both lysis of heat-inactivated CMV virions (EDX CMV panel) and isothermal amplification of released CMV DNA in spiked urine (~11 minutes), while no CMV DNA amplification was observed using NEB's standard LAMP buffer (FIG. 9). Of note, lysis buffer components added to NEB's standard LAMP buffer resulted in late-cycle (28 minutes) detection of CMV DNA amplification products. Thus, the data indicate that without a prior nucleic acid extraction step amplification of the target pathogen sequence cannot occur.

The TS solution disclosed above is compatible and can be used directly with standard methods of nucleic acid (RNA or DNA) amplification, such as PCR or RT-PCR. Exemplary protocols for PCR and RT-PCR are shown below.

| Component | 25 μl Reaction | Final Concentration |
| --- | --- | --- |
| Nuclease-free water | to 25 μl | |
| 10 μM Forward Primer | 1.25 μl | 0.5 μM |
| 10 μM Reverse Primer | 1.25 μl | 0.5 μM |
| Template DNA | 5.0 ul cDNA or alternatively 5 ul inoculated PTM if using single-step RT-PCR | |

-continued

| Component | 25 μl Reaction | Final Concentration |
| --- | --- | --- |
| Phusion Hot Start Flex 2X Master Mix | 12.5 μl | 1X |
| Eva Green | 1.0 ul | 1X |

Notes:
gently mix the reaction. Collect all liquid to the bottom of the tube by a quick spin if necessary. Overlay the sample with mineral oil if using a PCR machine without a heated lid.

Transfer PCR tubes to a PCR machine and begin thermocycling. Phusion Hot Start Flex DNA Polymerase does not require a separate activation step. Standard Phusion cycling conditions are recommended. Thermocycling conditions for a routine PCR are shown below:

| Step | Temperature | Duration |
| --- | --- | --- |
| Initial denaturation: | 98° C. | 30 seconds |
| 25-30 cycles: | 98° C. | 10 seconds |
| | 55° C. | 20 seconds |
| | 72° C. | 20 seconds |

General Guidelines:

Template: use of high quality, purified DNA templates greatly enhances the success of PCR. Recommended amounts of DNA template for a 50 μl reaction are as follows:

| DNA | Amount |
| --- | --- |
| Genomic | 50 ng-250 ng |
| Plasmid or viral | 1 pg-10 ng |

If the template DNA is obtained from a cDNA synthesis reaction, the volume added should be less than 10% of the total reaction volume. Primers: oligonucleotide primers are generally 20-40 nucleotides in length and ideally have a GC content of 40-60%. Computer programs such as Primer3 (Untergasser A, et al., (2012) Primer3—new capabilities and interfaces. Nucleic Acids Research 40(15):e115) can be used to design or analyze primers. The final concentration of each primer in a PCR experiment using Phusion Hot Start Flex DNA Polymerase may be 0.2-1 μM, while 0.5 μM is strongly recommended. Mg$^{++}$ and additives: at 1× concentration, Phusion Hot Start Flex Master Mix provides 1.5 mM MgCl$_2$ and 200 μM of each dUTP in the final reaction. Phusion Hot Start Flex DNA Polymerase cannot incorporate dUTP and is not recommended for use with uracil-containing primers or template. Amplification of difficult targets, such as those with GC-rich sequences or secondary structure, may be improved by the presence of additives such as DMSO (included). A final concentration of 3% DMSO is recommended, although concentration can be optimized in 2% increments. It is important to note that if a high concentration of DMSO is used, the annealing temperature must be lowered as DMSO decreases the primer $T_m$ (2). Phusion Hot Start flex 2× Master Mix is also compatible with other additives such as formamide or glycerol.

Phusion Hot Start Flex DNA Polymerase Concentration: the concentration of Phusion Hot Start Flex DNA Polymerase in the Phusion Hot Start Flex 2× Master Mix has been optimized for best results under a wide range of conditions. If reactions are set up according to recommendations listed, the final concentration of Phusion Hot Start Flex DNA Polymerase is 1 unit/50 μl reaction or 0.5 units/25

µl reaction. Denaturation: Phusion Hot Start Flex DNA Polymerase does not require a separate activation step. An initial denaturation of 30 seconds at 98° C. is sufficient for most amplicons from pure DNA templates. Longer denaturation times can be used (up to 3 minutes) for templates that require it. During thermocycling, the denaturation step should be kept to a minimum. Typically, a 5-10 second denaturation at. 98° C. is recommended for most templates. Cycle number: Generally, 25-35 cycles yield sufficient product. Testing by TaqMan real-time RT-PCR can be carried out using specifically designed primers and probes. Alternatively, predesigned TaqMan Assays can be used available from Applied Biosystems/Thermo Fischer Scientific. Real-time RT-PCR can be carried out on an ABI 7900HT instrument using AmpliTaq Gold (Life Technologies, CA, USA), Revertaid reverse transcriptase (Fermentas), dNTP, MgCl2, primers, 100 nM probe and RNA. Cycling conditions can be different, for example, 30 min at 48° C. and 10 min at 95° C. followed by 40 cycles of 15 s at 95° C. and 1 min at 60° C. Reactions containing water instead of RNA can be included in each run as negative controls. Results are interpreted in terms of Ct (cycle threshold) values.

EXAMPLES

Aspects of the present teachings may be further understood in light of the following examples, which should not be construed as limiting the scope of the present teachings in any way. Primers used in the following examples are listed in Table 1.

Example 1. RT-LAMP-Dependent Amplification of a Nucleic Acid from Biological Samples Containing CMV Virus To amplify RNA under isothermal conditions without non-target amplification, the optimized RT-LAMP reaction and Bst 3.0 DNA polymerase were utilized. Bst 3.0 DNA polymerase has improved isothermal amplification performance and strong reverse transcription at elevated temperatures (up to 72° C.), so that total reaction time was reduced to 30 min, and addition of exogenous reverse transcriptase is optional. The stability of Bst 3.0 at elevated temperatures minimizes non-target amplification problem by preventing the formation of primer dimers. Initial reactions were carried out in a total 25 µl reaction volume containing approximately 50 pmol each of the forward and backward internal primers, 25 pmol each of forward and backward loop primers in a amplification reaction mixture having 20 mM Tris-HCl, pH=8.8, 2 mM MgSO₄, 50-150 mM KCl (depending on polymerase), 1.4 mM dNTPs, 0.1% Tween 20, 8 units of the Bst DNA polymerase (NEB), 300 µM BSA, 0.1-1.0% Triton X-100. The primer sequences used for CMV virus detection are indicated in Table 1 (SEQ ID NO: 1-4). Positive and negative controls were included in each run, and all precautions to prevent cross-contamination were observed. The optimum temperature for the isothermal amplification reaction was found to be 68° C. After mixing and incubating for 2 min, amplification and preliminary detection (one minute read increments) was carried out in a single step (dsDNA dye) using a MX3005P instrument and software. Alternatively, a portable isothermal instrument (EseQuant TS2) was used.

For RT-LAMP, 1 ul (15 units) of WarmStart RTx reverse transcriptase (NEB) was added to the reaction mixture (thus replacing 1 ul H₂O). RT-LAMP reaction was carried out in a 30 µL reaction mixture containing 1× Amplification reaction mixture (20 mM Tris-HCl, 50 mM KCl, 2 mM MgSO4, 0.3% Tween® 20, 2 mM MgSO4, 300 µM bovine serum albumin (BSA), 0.1-1.0% Triton X-100, 1.4 mM dNTP mix, 1.28 uM FIP/BIP primers, 0.64 uM Loop primers, 8 units Bst 3.0 DNA polymerase, 15 units RTase (reverse transcriptase)).

An exemplary lateral flow assay (LFA) platform contains a buffer loading pad, a conjugate pad, a test line, a control line, and an absorbent pad. In one embodiment, streptavidin-coated gold nanoparticles (AuNPs) are gathered in the conjugate pad, and anti-digoxigenin and biotin are also affixed at the test line and control line, respectively. First, about 1 µL of digoxigenin and biotin-labeled RT-LAMP products are loaded into the conjugate pad, so that the biotin-labeled RT-LAMP products formed a complex with AuNPs via streptavidin-biotin interactions. Next, about 45 µL of diluent buffer are added to the buffer loading pad, and the capillary flow transfers AuNPs from the conjugate pad to the test and control line. The AuNP/RT-LAMP complexes are immobilized at the test line by interaction between digoxigenin and anti-digoxigenin, whereas the AuNPs that did not form complexes are captured by biotin. Complexed and non-complexed AuNPs are indicated by colored bands at the test and control line, respectively. The colorimetric signals are easily visible to the naked eye within 5 min.

Example 2. LAMP was Carried Out Using Labelled Primers

For this experiment, LAMP reactions were incubated in a heated block. For each assay, one loop primer (B-loop) was labelled with biotin, and the other loop primer (F-loop) was labelled with either FITC, DIG or Texas Red. LAMP using labelled primers resulted in amplification products labelled with two ligands, allowing the products to be detected by the Lateral Flow device. PCRD-4 devices containing reagents to bind to FITC, DIG and Texas Red on the membrane and latex functionalized to bind to biotin were obtained from Forsite Diagnostics (York, UK). The labelled LAMP reactions were diluted in LFD dilution buffer (Forsite Diagnostics). Approximately 70 ul of the diluted reactions were applied to the release pad of the device. The presence of detectable levels was indicated by the presence of a line at the corresponding position of the device: position 1: DIG-labelled product; position 2: Texas Red-labelled product; position 3: FITC-labelled product.

Example 3. Comparison of Amplification Efficiency of the Amplification Solution in Comparison with the Commercially Available (NEB) LAMP Formulation LAMP amplification of heat-inactivated CMV-spiked urine (5 ul) was performed using CMV LAMP primers with the amplification solution (SEQ ID NO: 1-4); the reaction was carried out at 68° C. in a total of 25 µl reaction volume containing approximately 50 pmol each of the CMV forward and backward internal primers, 25 pmol each of forward and backward CMV loop primers, 20 mM Tris-HCl pH8.8, 10 mM (NH4)2SO4, 2 mM MgSO4, 50 mM KCl, 1.4 mM dNTPs, 0.1% Tween 20, 8 units Bst DNA polymerase, 300 uM BSA, 1× EvaGreen dye, and 1% Triton X-100 (FIG. 9, A). To show importance of Triton X-100 and BSA in the amplification reaction mixture, CMV LAMP primers with NEBs colorimetric LAMP mix with 1% Triton X-100 and 300 uM BSA (the optimized lysis conditions) was used (FIG. 9, B). For comparison, CMV LAMP primers with NEBs colorimetric LAMP mix buffer only was used (no Triton X-100 or BSA, FIG. 9, C). The results indicate that the described above isothermal reaction buffer has good lysis properties, as well as greater amplification efficiency (i.e., amplicon concentration difference as shown by the arrowheads at the 30 min mark). After mixing and incubating for 2 min, amplification and preliminary detection (one minute read increments) was carried out in a single step using a MX3005P instrument and software. Each cycle was 1 minute long. Long bar indicates positive fluorescence threshold (5000 RFU) using Eva green. Similar results were found for saliva (not shown).

Importantly, the addition of urine (low pH) to NEBs colorimetric LAMP mix immediately shifted the color from pink to yellow (normally indicating a positive sample) even before the incubation took place. Therefore, samples that can have low pH may not be suitable with colorimetric assays that depend on pH shift to determine sample results.

Figure 10:
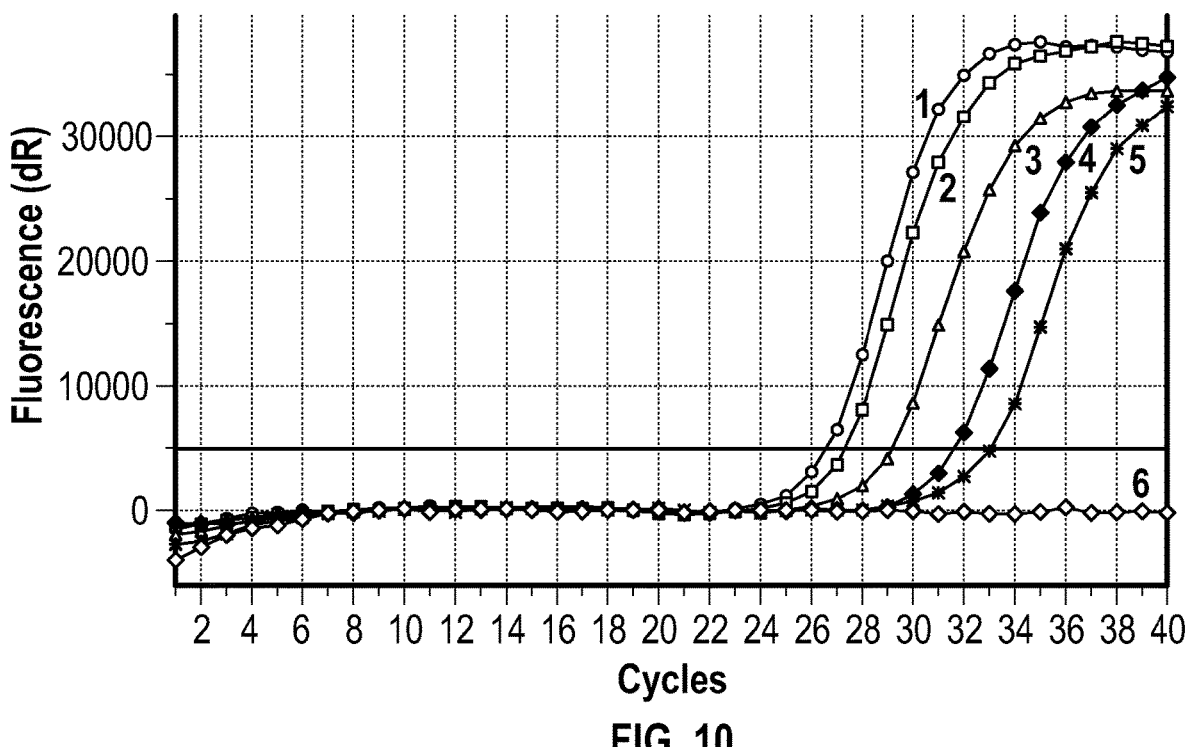
FIG. 10. Evaluating addition of BSA to increase efficiency of isothermal amplification. Various concentrations of BSA were added to the reaction mixtures: 1) 300 uM, 2) 240 uM, 3) 180 uM, 4) 120 uM, 5) 60 uM, and 6) OuM. LAMP amplification of purified CMV DNA was performed in the amplification reaction mixture.

Example 4. Evaluating Addition of BSA to Increase Efficiency of Isothermal Amplification Various concentrations of BSA were added to the reaction mixtures: 1) 300 uM, 2) 240 uM, 3) 180 uM, 4) 120 uM, 5) 60 uM, and 6) 0 uM. LAMP amplification of purified CMV DNA (1 ul) was performed in the following amplification reaction mixture: 50 pmol each of the CMV forward and backward internal primers, 25 pmol each of forward and backward CMV loop primers, 20 mM Tris-HCl pH8.8, 10 mM (NH4)2SO4, 2 mM MgSO4, 50 mM KCl, 1.4 mM dNTPs, 0.1% Tween 20, 8 units Bst DNA polymerase, and 1× EvaGreen dye (FIG. 10). The total reaction volume was 25 ul. The results in FIG. 10 indicate that BSA was able to enhance DNA amplification in a dose-dependent fashion. A 200-300 uM range was chosen as an optimal addition to the Amplification solution, since the amplification speed between 240 uM and 300 uM were very close, indicating the BSA was near optimal concentration. Higher concentrations were not tested (due to solubility and other factors) but may be possible with this system.

Figure 11:
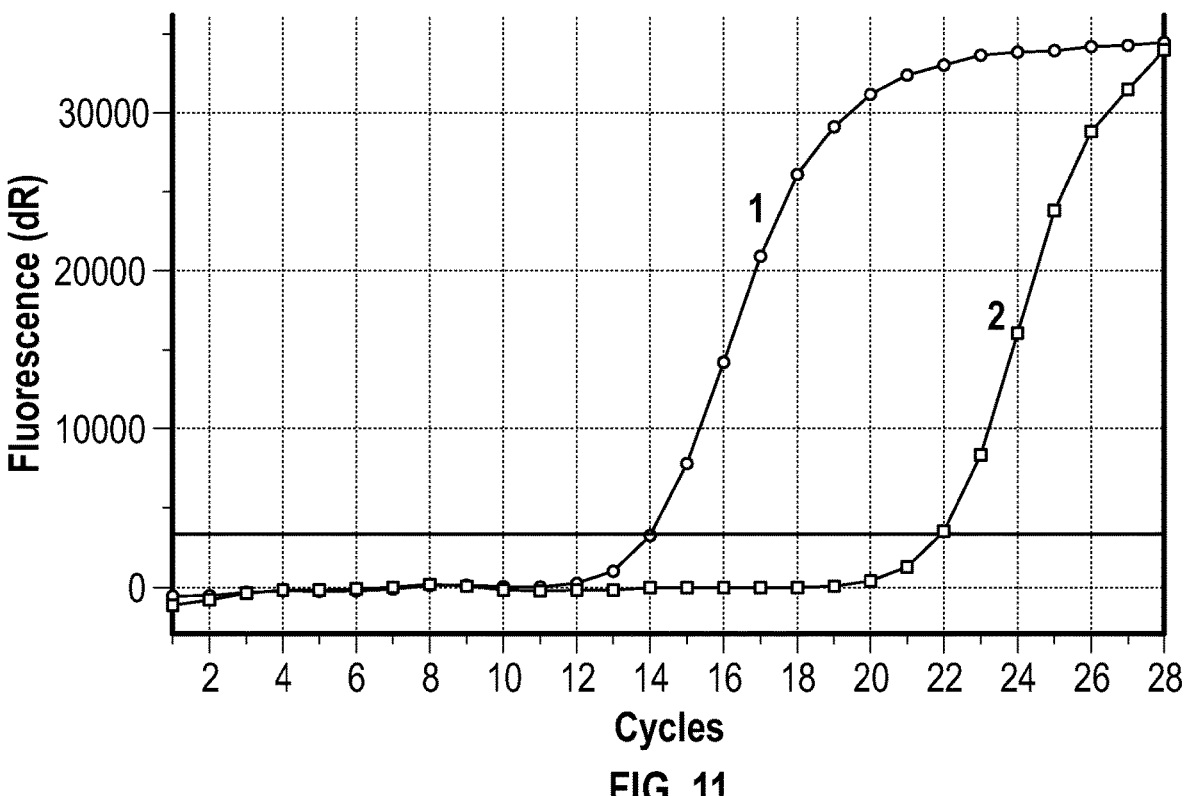
FIG. 11. Demonstrating the efficacy of BSA addition into the LAMP amplification mixture for HSV-1 detection in a clinical specimen from Baylor College of Medicine. Reaction mixture (1) contained 300 uM BSA, whereas reaction mixture (2) contained 0 uM BSA.

Example 5. Demonstrating the Efficacy of BSA Addition into Amplification Mixture for HSV-1 Detection in a Clinical Specimen from Baylor College of Medicine Amplification reactions were carried out in a total of 25 μl reaction volume containing approximately 50 pmol each of the HSV-1 forward and backward internal primers, 25 pmol each of forward and backward HSV-1 loop primers (see Table 1, SEQ ID NO: 17-20), 20 mM Tris-HCl pH 8.8, 10 mM (NH4)2SO4, 2 mM MgSO4, 50 mM KCl, 1.4 mM dNTPs, 0.1% Tween 20, 8 units Bst DNA polymerase, 1× EvaGreen dye, and 1% Triton X-100. Reaction mixture (1) contained 300 uM BSA, whereas reaction mixture (2) contained 0 uM BSA (FIG. 11). The addition of 300 uM BSA reduced the time of detection by 8 minutes (36% faster).

Figure 12:
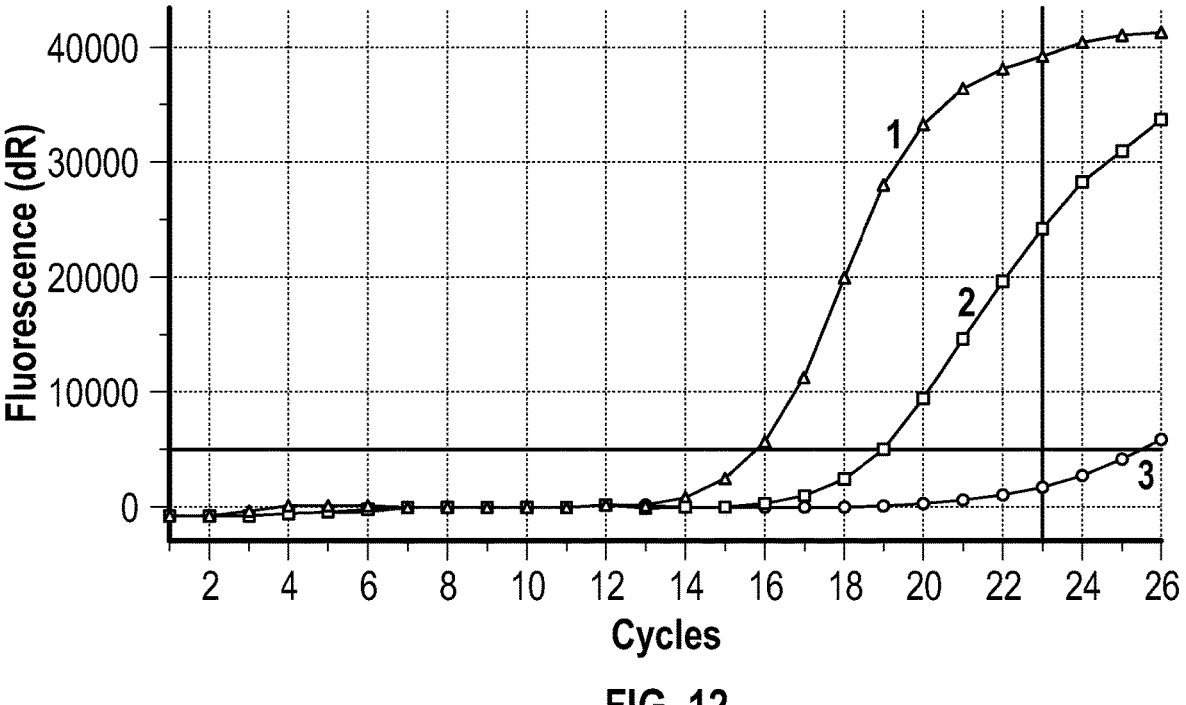
FIG. 12. Increasing the LAMP assay efficiency by adjusting $MgSO_4$ concentration in the amplification mixture. The LAMP assay reactions for CMV detection were carried out with a standard Amplification Solution and have varying concentrations of MgSO4: 1-2 mM, 2-4 mM; 3-6 mM. 3 was considered negative for amplification within the 23 minute cutoff with the standardized test procedure.

Example 6. Increasing the LAMP Assay Efficiency by Adjusting MgSO4 Concentration The LAMP assay reactions were carried out in a total of 25 μl reaction volume containing approximately 50 pmol each of the CMV forward and backward internal primers, 25 pmol each of forward and backward CMV loop primers, 20 mM Tris-HCl pH 8.8, 10 mM (NH4)2SO4, 50 mM KCl, 1.4 mM dNTPs, 0.1% Tween 20, 8 units Bst DNA polymerase, 300 uM BSA, ix EvaGreen dye, and 1% Triton X-100, The reactions had the following amounts of MgS04: Reaction 1-2 mM, Reaction 2-4 mM; Reaction 3-6 mM (FIG. 12). The addition of MgSO4 to the reactions at concentrations greater than 2 mM resulted in reduced amplification speed (FIG. 12). Reaction 3 was considered negative for amplification within the 23 minute cutoff with the standardized test procedure for CMV detection. Thus, higher MgSO4 concentrations, normally associated with standard isothermal LAMP assay, can be inhibitory in combination with the amplification solution components. Optimal MgSO4 concentration for the assay was estimated to be within 2-4 mM range.

Example 7. Increasing the LAMP Assay Efficiency by Adjusting Triton X-100 Concentration The LAMP assay reactions were carried out in a total of 25 μl reaction volume containing approximately 50 pmol each of the EBV forward and backward internal primers, 25 pmol each of forward and backward EBV loop primers (SEQ ID NO: 9-12), 20 mM Tris-HCl pH 8.8, 10 mM (NH4)2SO4, 50 mM KCl, 1.4 mM dNTPs, 0.1% Tween 20, 8 units Bst DNA polymerase, 300 uM BSA, and 1× EvaGreen dye. The reactions had the following final concentrations of Triton X-100: Reaction 1—1%, Reaction 2—4%; Reaction 3—16% (FIG. 12). The addition of Triton X-100 greater than 2% (1% final in reaction mixture) resulted in reduced amplification speed and reduced amplicon production (RFU). Optimal Triton X-100 concentration for amplification was estimated to be within 1-2% range, however, the amplification assay efficiency did not drop dramatically even with 16% Triton X-100. In addition, higher Triton X-100 concentrations can be beneficial for pathogen inactivation. Therefore, different concentration ranges from 1 to 16% of Triton X-100 can be utilized in the amplification mixture for different pathogens and different assays. Concentration of Triton X-100 in Transport Solution (TS) can be formulated accordingly (typically, twice higher than in the amplification mixture).

Similar data were obtained with another non-ionic detergent, Tween-20 (data not shown). Thus, Tween-20 can be utilized as a substitute for Triton X-100 in Transport Solution (TS).

Example 8. a LAMP Assay to Detect Epstein-Barr Virus (EBV), a Medically Important Herpesvirus that Causes Infectious Mononucleosis, Malignant Lymphomas and Nasopharyngeal Carcinoma In this example, the LAMP and qPCR methods were compared using the same dilutions of EBV DNA and the same fluorescent reporter (EvaGreen dye) measured in an MX3005P real-time PCR instrument. LAMP conditions were the same as in Example 6 with 2 mM MgS04. LAMP primers and qPCR (BALF5 primers in Table 1, SEQ ID NO: 9-12) were used to amplify serially-diluted EBV DNA (range 10,000 copies to 10 copies). LAMP primers detected $10^4$ copies of EBV DNA in 16 min (19 min for $10^3$ copies of EBV DNA), while the qPCR method required 40 min to detect $10^4$ copies (46 min for $10^3$ copies; not taking into account additional 10 min at 95° C. step to activate the Taq polymerase used for the PCR), see FIG. 14. These data show that: 1) LAMP is faster than PCR for target detection, 2) LAMP is applicable to relative quantitation nearly identical to PCR.

Example 9. Detection of Human Herpesvirus-8 or
Kaposi's Sarcoma Virus (HHV-8 or KSHV)

The LAMP assay reactions were carried out to amplify the
ORF73 gene of HHV-8 for detection of KSHV. LAMP
conditions were the same as in Example 6 with 2 mM
MgSO4. Primers were as disclosed in Table 1, SEQ ID NO:
37-40. Pathogen was obtained from a swab in the TS.
Positive identification results (FIG. 15) were obtained in 14
minutes. Line 1 indicates positive amplification. The nega-
tive control did not amplify (Line 2).

Example 10. Amplifying a nucleic acid molecule of
a pathogen contained in a Dried Blood Spot (DBS)

Figures 16A, 16B, 16C, 16D:
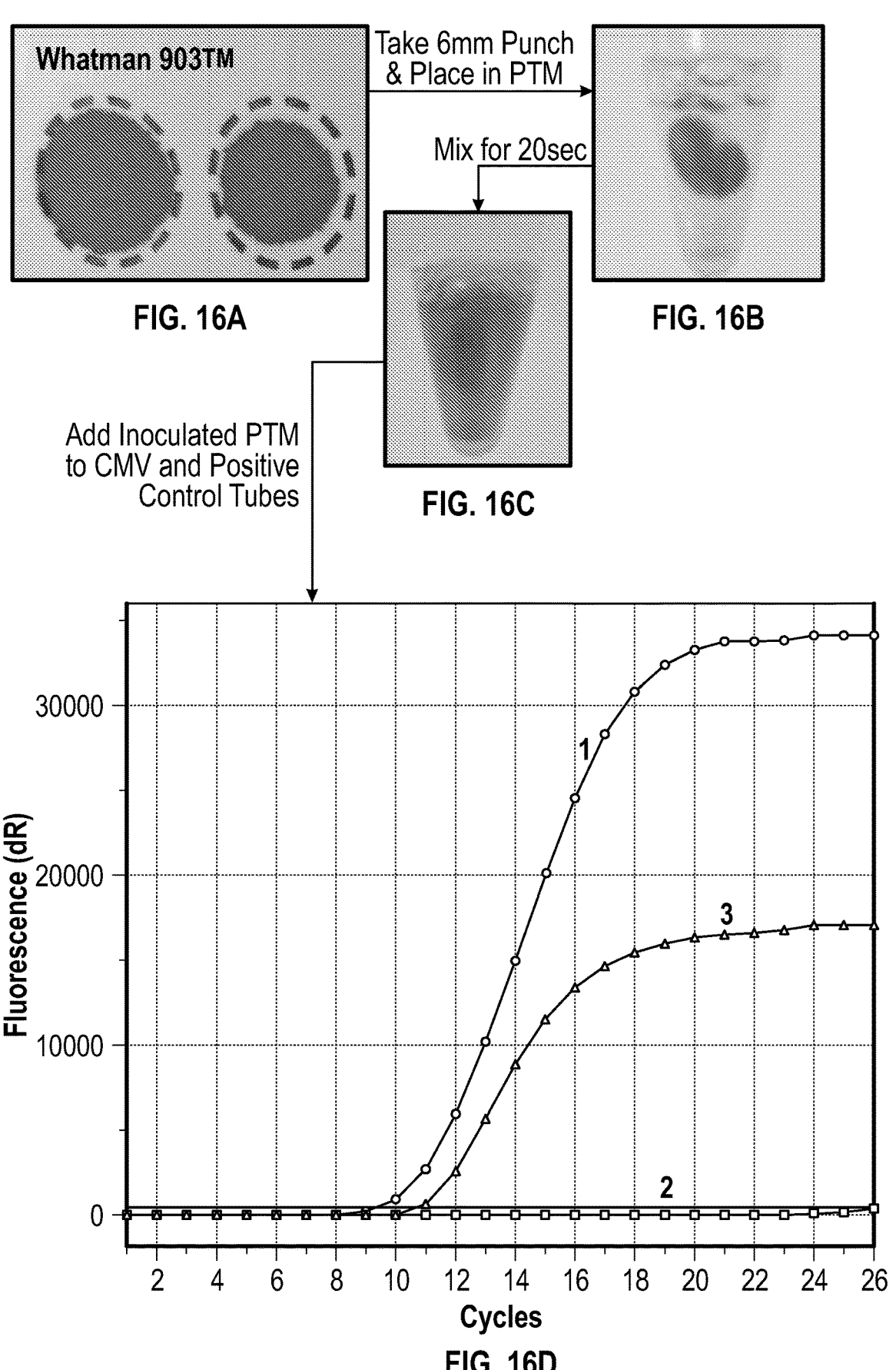
FIG. 16A-D. Amplifying a nucleic acid molecule of a pathogen contained in a Dried Blood Spot (DBS). Contrived DBS samples were prepared by spiking 10 ul CMV AD169 culture harvest virus into 200 ul whole blood. FTA cards were then spotted with 30 ul spiked whole blood and air dried for 4 hrs (FIG. 16A). Punches (6 mm) were then placed into 400 ul TS (FIG. 16B) and vortexed for 20 seconds (FIG. 16C). Inoculated TS (25 ul) was immediately pipetted into the CMV and positive control test tubes (a synthetic Lambda DNA construct) for a total reaction volume of 50 ul; non-spiked whole blood served as a negative control.

This example shows isothermal amplification data for
nucleic acid molecules derived from CMV-contained DBS
samples. Contrived DBS samples were prepared by spiking
10 ul CMV AD169 culture harvest virus into 200 ul whole
blood. FTA cards were then spotted with 30 ul spiked whole
blood and air dried for 4 hrs (FIG. 16A). Punches (6 mm)
were then placed into 400 ul TS (FIG. 16B) and vortexed for
20 seconds (FIG. 16C). Inoculated TS (25 ul) was immedi-
ately pipetted into the CMV and positive control test tubes
(a synthetic Lambda DNA construct) for a total reaction
volume of 50 ul; non-spiked whole blood served as a
negative control. As shown in FIG. 16D, the CMV+ DBS
sample (line 1) was positive while the CMV-DBS sample
(line 2) was negative. The positive control (line 3) also
showed positive amplification. The liquid buffer CMV+
samples were also positive, indicating there was no appre-
ciable DNA loss as a result of the DBS preparation proce-
dure (data not shown). In addition, tested duplicate DBS
samples were tested that were stored for 59 days at room
temperature, and a positive CMV result was again observed.
Overall, the total time from punching the FTA card to CMV
test results was less than 25 minutes.

Figure 17:
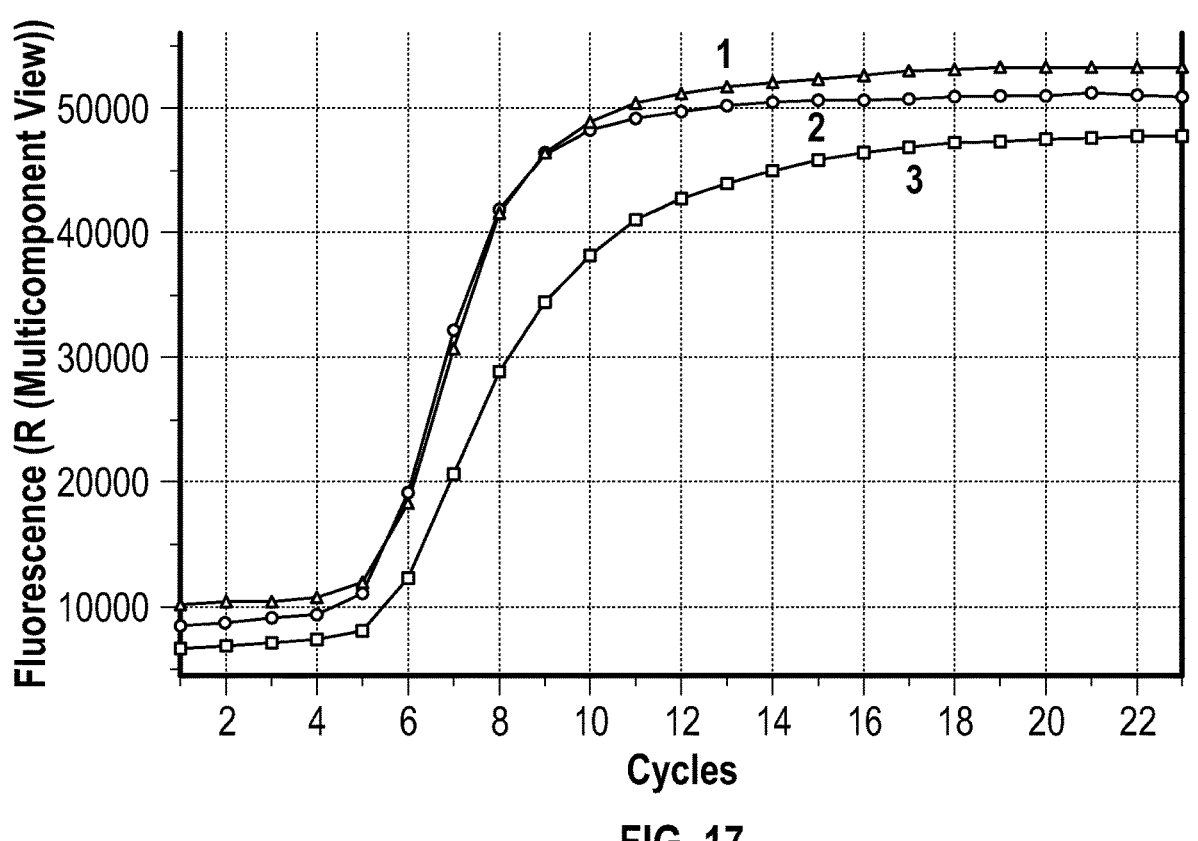
FIG. 17. Evaluating addition of ammonium sulfate or a second detergent Tween-20 into the amplification reaction mixture to increase amplification efficiency.

Example 11. Evaluating Addition of Ammonium
Sulfate or a Second Detergent Tween-20 into the
Amplification Reaction Mixture to Increase
Amplification Efficiency The LAMP assay reactions were carried out as described
in Example 6. The amplification reaction mixture comprised
the following buffer: 20 mM Tris-HCl pH 8.8, 10 mM
(NH4)2SO4 (if present), 50 mM KCl, 1.4 mM dNTPs, 0.1%
Tween-20 (if present), 8 units Bst DNA polymerase, 300 uM
BSA, 1% Triton X-100, and 1× EvaGreen dye. Reactions
were carried out at 68° C. in a total of 25 µl reaction volume
containing approximately 50 pmol each of the EBV forward
and backward internal primers, 25 pmol each of forward and
backward EBV loop primers. FIG. 17 shows amplification
results for EBV pathogen kept in the TS before amplification
using three different buffer conditions: Reaction 1—buffer
with ammonium sulfate and Tween-20; Reaction 2—buffer
with Tween-20 but no ammonium sulfate; Reaction 3—buf-
fer with no Tween-20 and no ammonium sulfate. There was
no significant difference between reaction with the buffer
with or without ammonium sulfate. Although addition of the
second detergent Tween-20 into the amplification reaction
mixture improved amplification speed, the EBV identifica-
tion can be performed without either ammonium sulfate or
Tween-20 in the described amplification reaction mixture.

Example 12. Evaluating Influence of Different
Detergents Used in the Transport Solution (TS) on
Amplification Efficiency of the HSV-1 Pathogen
from Clinical Samples Four different non-ionic detergents present in the TS
(concentration for each detergent was 2%) were evaluated in the described LAMP amplification assay. An HSV-1 clinical
isolate was incubated in the TS containing one of the
detergents for 2 days. Aliquots of the TS contained the
pathogen were added to the amplification solution and
amplified using the LAMP assay. The reactions were carried
out in a total of 25 µl reaction volume containing approxi-
mately 50 pmol each of the HSV-1 forward and backward
internal primers, 25 pmol each of forward and backward
HSV-1 loop primers, 20 mM Tris-HCl pH8.8, 10 mM
(NH4)2SO4, 2 mM MgSO4, 50 mM KCl, 1.4 mM dNTPs,
0.1% Tween 20, 8 units Bst DNA polymerase, 300 uM BSA,
1× EvaGreen dye, and 1% of each of the detergents (the
amplification reaction mixture). Primers were as disclosed in
Table 1, SEQ ID NO: 17-20. FIG. 18A shows initial testing
of four different detergents after inoculating an HSV-1
clinical isolate into the TS containing 2% detergent and
immediate amplification. FIG. 18B shows comparison of
LAMP amplification after inoculating the HSV-1 clinical
isolate into the TS containing 2% detergent and storing for
2 days at room temperature before amplification to evaluate
stability of the viral DNA with each detergent. The results
show that the tested non-ionic detergents can be substituted
in the TS and in the amplification reaction mixture without
appreciable loss of amplification.

Other Embodiments

The detailed description set-forth above is provided to aid
those skilled in the art in practicing the present invention.
However, the invention described and claimed herein is not
to be limited in scope by the specific embodiments herein
disclosed because these embodiments are intended as illus-
tration of several aspects of the invention. Any equivalent
embodiments are intended to be within the scope of this
invention. Indeed, various modifications of the invention in
addition to those shown and described herein will become
apparent to those skilled in the art from the foregoing
description which do not depart from the spirit or scope of
the present inventive discovery. Such modifications are also
intended to fall within the scope of the appended claims.

REFERENCES CITED

All publications, patents, patent applications and other
references cited in this application are incorporated herein
by reference in their entirety for all purposes to the same
extent as if each individual publication, patent, patent appli-
cation or other reference was specifically and individually
indicated to be incorporated by reference in its entirety for
all purposes. Citation of a reference herein shall not be
construed as an admission that such is prior art to the present
invention.

Specifically intended to be within the scope of the present
invention, and incorporated herein by reference in its
entirety, are the following publications:

Notomi T, Okayama H, Masubuchi H, et al. Loop-medi-
ated isothermal amplification of DNA. Nucleic Acids
Res 2000; 28: E63.
Smyrlaki, et al. Massive and rapid COVID-19 testing is
feasible by extraction-free SARS-CoV-2 RT-qPCR.
medRxiv preprint doi: https://doi.org/10.1101/
2020.04.17.20067348.
Kaneko H, Iida T, Aoki K, Ohno S, Suzutani T. Sensitive
and rapid detection of herpes simplex virus and vari-
cella-zoster virus DNA by loop-mediated isothermal
amplification. J Clin Microbiol 2005; 43:3290-6.
Kaarj, K. et al., Sensitive Zika Virus Assay Using Smart-
phone Detection of Loop-mediated Isothermal Ampli-
fication on Paper Microfluidic Chips. Sci. Rep. 2018.

What is claimed is:

1. A method for amplifying a nucleic acid molecule of a pathogen contained in a biological sample in less than 30 min, the method comprising:

(a) obtaining a stabilized sample, the stabilized sample comprising the biological sample and a transport solution, wherein the transport solution comprises a non-ionic or zwitterionic detergent at a concentration of 2 to 32 percent (vol./vol.), and wherein the transport solution stabilizes the nucleic acid molecule in the stabilized sample at room temperature;

(b) mixing the stabilized sample with an amplification solution without prior extraction of the nucleic acid molecule present in the stabilized sample to form an amplification reaction mixture, wherein the amplification reaction mixture comprises:

a buffering agent that has a pH between about 5 and about 11;

serum albumin at a concentration of 100 μM to 500 μM;

the non-ionic or zwitterionic detergent at a concentration of 1 to 16 percent (vol./vol.);

$M_2SO_4$ at a concentration of 0.5 mM to 3 mM:

dNTPs, a DNA polymerase enzyme having a strand displacement activity selected from the group consisting of Bst polymerase and Bsm polymerase, and at least one pair of primers that target the nucleic acid molecule; and (c) subjecting the amplification reaction mixture to an isothermal amplification, wherein the isothermal amplification amplifies the nucleic acid molecule.

2. The method of claim 1, wherein the transport solution further comprises a buffering agent that has a pH between about 5 and about 11, and a chelating agent.

3. The method of claim 1, wherein the transport solution stabilizes the nucleic acid in the stabilized sample at room temperature for at least four weeks.

4. The method of claim 1, wherein the pathogen is selected from the group consisting of: an enveloped virus, pathogenic yeast and bacteria.

5. The method of claim 1, wherein the amplification reaction mixture comprises MgSO4 at a concentration of 2 mM.

6. The method of claim 1, wherein the amplification reaction mixture comprises at least two pairs of primers that target the nucleic acid molecule, and the isothermal amplification is a strand displacement amplification, a multiple displacement amplification, a recombinase polymerase amplification, a helicase dependent amplification, a rolling circle amplification, or a loop-mediated isothermal amplification.

7. The method of claim 1, wherein the nucleic acid molecule is a ribonucleic acid (RNA) and a corresponding DNA molecule is produced from the RNA by a reverse transcriptase enzyme prior to or simultaneously with the isothermal amplification.

8. The method of claim 1, wherein the biological sample is saliva, a nasal swab containing the pathogen, urine, lesion exudate, dried blood spot, blood, plasma/serum, mucus, vaginal fluid or another type of bodily fluid.

9. The method of claim 1, wherein the transport solution consists essentially of the non-ionic or zwitterionic detergent at a concentration of 2 to 32 percent (vol./vol.).

10. The method of claim 1, wherein the non-ionic or zwitterionic detergent is selected from the group consisting of: octylphenol ethoxylate, nonylphenol ethoxylate, octylphenol ethoxylate, polyoxyethylene (20) sorbitan monolaurate, polyoxyethylene (20) sorbitan monooleate, 3-[(3-cholamidopropyl)dimethylammonio]-1-propane-sulfonate, 3-[(3-cholamidopropyl)dimethylammonio]-2-hydroxy-1-propanesulfonate, and a mixture thereof.

11. The method of claim 1, wherein the non-ionic or zwitterionic detergent is present in the amplification reaction mixture at a concentration of 2 to 5 percent (vol./vol.).

12. A method for detecting a presence of a pathogen in a biological sample in less than 30 min, comprising:

(a) obtaining a stabilized sample, the stabilized sample comprising the biological sample and a transport solution, wherein the transport solution comprises a non-ionic or zwitterionic detergent at a concentration of 2 to 32 percent (vol./vol.), and wherein the transport solution stabilizes the nucleic acid molecule in the stabilized sample at room temperature;

(b) mixing the stabilized sample with an amplification solution without prior extraction of the nucleic acid molecule present in the stabilized sample to form an amplification reaction mixture, wherein the amplification reaction mixture comprises:

a buffering agent that has a pH between about 5 and about 11;

serum albumin at a concentration of 100 μM to 500 μM;

the non-ionic or zwitterionic detergent at a concentration of 1 to 16 percent (vol./vol.);

$MgSO_4$ at a concentration of 0.5 mM to 3 mM;

dNTPs, a DNA polymerase enzyme having a strand displacement activity selected from the group consisting of Bst polymerase and Bsm polymerase, and at least one pair of primers that target the nucleic acid molecule; and (c) subjecting the amplification reaction mixture to an isothermal amplification, wherein the isothermal amplification amplifies the nucleic acid molecule of the pathogen; and (d) detecting a presence of the amplified nucleic acid molecule by at least one of the following: colorimetric readout, fluorescent readout, lateral flow assay, a biosensor, wherein the presence of the amplified nucleic acid molecule indicates the presence of the pathogen in the biological sample.

13. A method for amplifying a nucleic acid molecule of a pathogen contained in a biological sample in less than 30 min, the method comprising:

(a) obtaining a stabilized sample, the stabilized sample consisting essentially of the biological sample and a transport solution, wherein the transport solution consists essentially of a non-ionic or zwitterionic detergent at a concentration of 2 to 32 percent (vol./vol.), and wherein the transport solution stabilizes the nucleic acid molecule in the stabilized sample at room temperature;

(b) mixing the stabilized sample with an amplification solution without prior extraction of the nucleic acid molecule present in the stabilized sample to form an amplification reaction mixture comprising the non-ionic or zwitterionic detergent at a concentration of 1 to 16 percent (vol./vol.), $MgSO_4$ at a concentration of 0.5 mM to 3 mM and Bst polymerase or Bsm polymerase; and (c) subjecting the amplification reaction mixture to an isothermal amplification, wherein the isothermal amplification amplifies the nucleic acid molecule.

14. The method of claim 13, wherein the non-ionic or zwitterionic detergent is selected from the group consisting of: octylphenol ethoxylate, nonylphenol ethoxylate, octylphenol ethoxylate, polyoxyethylene (20) sorbitan monolaurate, polyoxyethylene (20) sorbitan monooleate, 3-[(3-cholamidopropyl)dimethylammonio]-1-propane-sulfonate f-HAP-S, 3-[(3-cholamidopropyl)dimethylam-monio]-2-hydroxy-1-propanesulfonate, and a mixture thereof.

15. The method of claim 13, wherein the transport solution stabilizes the nucleic acid in the stabilized sample at room temperature for at least four weeks.

16. The method of claim 13, wherein the nucleic acid molecule is a ribonucleic acid (RNA) and a corresponding DNA molecule is produced from the RNA by adding a reverse transcriptase enzyme prior to or simultaneously with the step (c).

17. The method of claim 13, wherein the non-ionic or zwitterionic detergent is present in the amplification reaction mixture at a concentration of 2 to 5 percent (vol./vol.).

* * * * *

SEQUENCE LISTING

<160> NUMBER OF SEQ ID NOS: 40

<210> SEQ ID NO 1
<211> LENGTH: 45
<212> TYPE: DNA
<213> ORGANISM: Artificial Sequence
<220> FEATURE:
<223> OTHER INFORMATION: CMV FIP

<400> SEQUENCE: 1
cgataaccac cgaacccgca atttttcctt tccctcggct tctca                        45

<210> SEQ ID NO 2
<211> LENGTH: 46
<212> TYPE: DNA
<213> ORGANISM: Artificial Sequence
<220> FEATURE:
<223> OTHER INFORMATION: CMV BIP

<400> SEQUENCE: 2
catgtacccc gtatgcatgg cctttgtaa agctcggcca tagtgt                        46

<210> SEQ ID NO 3
<211> LENGTH: 18
<212> TYPE: DNA
<213> ORGANISM: Artificial Sequence
<220> FEATURE:
<223> OTHER INFORMATION: CMV LF

<400> SEQUENCE: 3
gtgctggccg gattgttg                                                      18

<210> SEQ ID NO 4
<211> LENGTH: 25
<212> TYPE: DNA
<213> ORGANISM: Artificial Sequence
<220> FEATURE:
<223> OTHER INFORMATION: CMV LB

<400> SEQUENCE: 4
aagactaact cgcccaacta taagc                                              25

<210> SEQ ID NO 5
<211> LENGTH: 45
<212> TYPE: DNA
<213> ORGANISM: Artificial Sequence
<220> FEATURE:
<223> OTHER INFORMATION: SARS-CoV-2 FIP

<400> SEQUENCE: 5
ccactgcgtt ctccattctg gtttttaaat gcaccccgca ttacg                        45

<210> SEQ ID NO 6
<211> LENGTH: 45
<212> TYPE: DNA
<213> ORGANISM: Artificial Sequence
<220> FEATURE:
<223> OTHER INFORMATION: SARS-CoV-2 BIP

<400> SEQUENCE: 6
cgcgatcaaa acaacgtcgg cttttccttg ccatgttgag tgaga                        45

<210> SEQ ID NO 7
<211> LENGTH: 25
<212> TYPE: DNA
<213> ORGANISM: Artificial Sequence

```
<220> FEATURE:
<223> OTHER INFORMATION: SARS-CoV-2 LF

<400> SEQUENCE: 7
cagttgaatc tgagggtcca ccaaa                                      25

<210> SEQ ID NO 8
<211> LENGTH: 24
<212> TYPE: DNA
<213> ORGANISM: Artificial Sequence
<220> FEATURE:
<223> OTHER INFORMATION: SARS-CoV-2 LB

<400> SEQUENCE: 8
ttacccaata atactgcgtc ttgg                                       24

<210> SEQ ID NO 9
<211> LENGTH: 44
<212> TYPE: DNA
<213> ORGANISM: Artificial Sequence
<220> FEATURE:
<223> OTHER INFORMATION: EBV BALF5 FIP

<400> SEQUENCE: 9
tcccatccca acagtgtgtg tcttttgatc cgacacccgt gctt                 44

<210> SEQ ID NO 10
<211> LENGTH: 44
<212> TYPE: DNA
<213> ORGANISM: Artificial Sequence
<220> FEATURE:
<223> OTHER INFORMATION: EBV BALF5 BIP

<400> SEQUENCE: 10
ggtgatcttg tggtagtcgc cgttttcggg tctcggtgga gaag                 44

<210> SEQ ID NO 11
<211> LENGTH: 17
<212> TYPE: DNA
<213> ORGANISM: Artificial Sequence
<220> FEATURE:
<223> OTHER INFORMATION: EBV BALF5 LF

<400> SEQUENCE: 11
gccacgtggc tgcaaga                                               17

<210> SEQ ID NO 12
<211> LENGTH: 17
<212> TYPE: DNA
<213> ORGANISM: Artificial Sequence
<220> FEATURE:
<223> OTHER INFORMATION: EBV BALF5 LB

<400> SEQUENCE: 12
gcatggttgc cgtagcc                                               17

<210> SEQ ID NO 13
<211> LENGTH: 41
<212> TYPE: DNA
<213> ORGANISM: Artificial Sequence
<220> FEATURE:
<223> OTHER INFORMATION: EBV IR FIP

<400> SEQUENCE: 13
agctgtccga ggggaccctt tttcaccaca cccaggcaca c                    41
```

-continued

```
<210> SEQ ID NO 14
<211> LENGTH: 43
<212> TYPE: DNA
<213> ORGANISM: Artificial Sequence
<220> FEATURE:
<223> OTHER INFORMATION: EBV IR BIP

<400> SEQUENCE: 14
gtcctaccag aggggggccat tttccgctta ccacctcctc ttc                    43

<210> SEQ ID NO 15
<211> LENGTH: 18
<212> TYPE: DNA
<213> ORGANISM: Artificial Sequence
<220> FEATURE:
<223> OTHER INFORMATION: EBV IR LF

<400> SEQUENCE: 15
cgggtgggtg tgtgtagt                                                 18

<210> SEQ ID NO 16
<211> LENGTH: 20
<212> TYPE: DNA
<213> ORGANISM: Artificial Sequence
<220> FEATURE:
<223> OTHER INFORMATION: EBV IR LB

<400> SEQUENCE: 16
agaacccaga cgagtccgta                                               20

<210> SEQ ID NO 17
<211> LENGTH: 42
<212> TYPE: DNA
<213> ORGANISM: Artificial Sequence
<220> FEATURE:
<223> OTHER INFORMATION: HSV-1 FIP

<400> SEQUENCE: 17
gtttttgccg cccatcaggc tgttttgcat ggccggcaac ga                      42

<210> SEQ ID NO 18
<211> LENGTH: 41
<212> TYPE: DNA
<213> ORGANISM: Artificial Sequence
<220> FEATURE:
<223> OTHER INFORMATION: HSV-1 BIP

<400> SEQUENCE: 18
ccttattttt gaccgcaccc gctttttaggc cgcgcacaca a                      41

<210> SEQ ID NO 19
<211> LENGTH: 18
<212> TYPE: DNA
<213> ORGANISM: Artificial Sequence
<220> FEATURE:
<223> OTHER INFORMATION: HSV-1 LF

<400> SEQUENCE: 19
tcccggcctg aaacacac                                                 18

<210> SEQ ID NO 20
<211> LENGTH: 20
<212> TYPE: DNA
<213> ORGANISM: Artificial Sequence
<220> FEATURE:
<223> OTHER INFORMATION: HSV-1 LB
```

-continued

<400> SEQUENCE: 20
aagttcgtcc tggcctgtcc                                                    20

<210> SEQ ID NO 21
<211> LENGTH: 40
<212> TYPE: DNA
<213> ORGANISM: Artificial Sequence
<220> FEATURE:
<223> OTHER INFORMATION: HSV-2 FIP

<400> SEQUENCE: 21
gtagtcccgg tccgcctcca tttttccagg cccacaacct                             40

<210> SEQ ID NO 22
<211> LENGTH: 41
<212> TYPE: DNA
<213> ORGANISM: Artificial Sequence
<220> FEATURE:
<223> OTHER INFORMATION: HSV-2 BIP

<400> SEQUENCE: 22
tggagatcga ggtggggggt tttgcagcag gatgctcagc a                           41

<210> SEQ ID NO 23
<211> LENGTH: 20
<212> TYPE: DNA
<213> ORGANISM: Artificial Sequence
<220> FEATURE:
<223> OTHER INFORMATION: HSV-2 LF

<400> SEQUENCE: 23
gggagagcgt actgaagcac                                                    20

<210> SEQ ID NO 24
<211> LENGTH: 21
<212> TYPE: DNA
<213> ORGANISM: Artificial Sequence
<220> FEATURE:
<223> OTHER INFORMATION: HSV-2 LB

<400> SEQUENCE: 24
ctgttcttcg tgaaggccca c                                                  21

<210> SEQ ID NO 25
<211> LENGTH: 45
<212> TYPE: DNA
<213> ORGANISM: Artificial Sequence
<220> FEATURE:
<223> OTHER INFORMATION: VZV FIP

<400> SEQUENCE: 25
agggccccgt gtaacatatc cattttttgt aggccttgca agtgc                       45

<210> SEQ ID NO 26
<211> LENGTH: 44
<212> TYPE: DNA
<213> ORGANISM: Artificial Sequence
<220> FEATURE:
<223> OTHER INFORMATION: VZV BIP

<400> SEQUENCE: 26
tcacggcctg ttatttcctc ggttttaggg tccaaaacca ctgc                        44

<210> SEQ ID NO 27

-continued

```
<211> LENGTH: 23
<212> TYPE: DNA
<213> ORGANISM: Artificial Sequence
<220> FEATURE:
<223> OTHER INFORMATION: VZV LF

<400> SEQUENCE: 27
ctcttttttc ttggcgttgg tac                                              23

<210> SEQ ID NO 28
<211> LENGTH: 22
<212> TYPE: DNA
<213> ORGANISM: Artificial Sequence
<220> FEATURE:
<223> OTHER INFORMATION: VZV LB

<400> SEQUENCE: 28
atgccaccaa acagtaaatc cc                                               22

<210> SEQ ID NO 29
<211> LENGTH: 39
<212> TYPE: DNA
<213> ORGANISM: Artificial Sequence
<220> FEATURE:
<223> OTHER INFORMATION: Chlamydia tri. FIP

<400> SEQUENCE: 29
tcgagcaacc gctgtgacga ccttcattat gtcggagtc                             39

<210> SEQ ID NO 30
<211> LENGTH: 39
<212> TYPE: DNA
<213> ORGANISM: Artificial Sequence
<220> FEATURE:
<223> OTHER INFORMATION: Chlamydia tri. BIP

<400> SEQUENCE: 30
gcagcttgta gtcctgcttg agtcttcgta actcgctcc                             39

<210> SEQ ID NO 31
<211> LENGTH: 18
<212> TYPE: DNA
<213> ORGANISM: Artificial Sequence
<220> FEATURE:
<223> OTHER INFORMATION: Chlamydia tri. LF

<400> SEQUENCE: 31
tacaaacgcc tagggtgc                                                    18

<210> SEQ ID NO 32
<211> LENGTH: 18
<212> TYPE: DNA
<213> ORGANISM: Artificial Sequence
<220> FEATURE:
<223> OTHER INFORMATION: Chlamydia tri. LB

<400> SEQUENCE: 32
cgggcgattt gccttaac                                                    18

<210> SEQ ID NO 33
<211> LENGTH: 47
<212> TYPE: DNA
<213> ORGANISM: Artificial Sequence
<220> FEATURE:
<223> OTHER INFORMATION: Candida alb. FIP

<400> SEQUENCE: 33
```

-continued

```
aacgacgctc aaacaggcat ttttcgtgaa tcatcgaatc tttgaac                    47

<210> SEQ ID NO 34
<211> LENGTH: 42
<212> TYPE: DNA
<213> ORGANISM: Artificial Sequence
<220> FEATURE:
<223> OTHER INFORMATION: Candida alb. BIP

<400> SEQUENCE: 34
ctgggtttgg tgttgagcaa ttttatcccg ccttaccact ac                         42

<210> SEQ ID NO 35
<211> LENGTH: 18
<212> TYPE: DNA
<213> ORGANISM: Artificial Sequence
<220> FEATURE:
<223> OTHER INFORMATION: Candida alb. LF

<400> SEQUENCE: 35
accagagggc gcaatgtg                                                    18

<210> SEQ ID NO 36
<211> LENGTH: 23
<212> TYPE: DNA
<213> ORGANISM: Artificial Sequence
<220> FEATURE:
<223> OTHER INFORMATION: Candida alb. LB

<400> SEQUENCE: 36
acgacttggg tttgcttgaa aga                                              23

<210> SEQ ID NO 37
<211> LENGTH: 45
<212> TYPE: DNA
<213> ORGANISM: Artificial Sequence
<220> FEATURE:
<223> OTHER INFORMATION: HHV-8 FIP

<400> SEQUENCE: 37
tcgctggatg atcccacgta gatttttgtg acttcgccaa ccgta                      45

<210> SEQ ID NO 38
<211> LENGTH: 42
<212> TYPE: DNA
<213> ORGANISM: Artificial Sequence
<220> FEATURE:
<223> OTHER INFORMATION: HHV-8 BIP

<400> SEQUENCE: 38
cgatactccg ccacgccaac ttttacccca ggatccctca ga                         42

<210> SEQ ID NO 39
<211> LENGTH: 17
<212> TYPE: DNA
<213> ORGANISM: Artificial Sequence
<220> FEATURE:
<223> OTHER INFORMATION: HHV-8 LF

<400> SEQUENCE: 39
gggactctgt ggcccat                                                     17

<210> SEQ ID NO 40
<211> LENGTH: 20
<212> TYPE: DNA
```

-continued

```
<213> ORGANISM: Artificial Sequence
<220> FEATURE:
<223> OTHER INFORMATION: HHV-8 LB

<400> SEQUENCE: 40
cgcctacatc tcccatctcc                                                      20
```